(12) United States Patent
Collazo et al.

(10) Patent No.: US 11,857,205 B2
(45) Date of Patent: Jan. 2, 2024

(54) VOID FILLING JOINT PROSTHESIS AND ASSOCIATED INSTRUMENTS

(71) Applicant: Howmedica Osteonics Corp., Mahwah, NJ (US)

(72) Inventors: Carlos E. Collazo, Old Greenwich, CT (US); Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 17/743,980

(22) Filed: May 13, 2022

(65) Prior Publication Data

US 2022/0273319 A1 Sep. 1, 2022

Related U.S. Application Data

(63) Continuation of application No. 16/694,113, filed on Nov. 25, 2019, now Pat. No. 11,357,518, which is a
(Continued)

(51) Int. Cl.
*A61F 2/38* (2006.01)
*A61B 17/16* (2006.01)
(Continued)

(52) U.S. Cl.
CPC ........ *A61B 17/1675* (2013.01); *A61B 17/164* (2013.01); *A61B 17/17* (2013.01);
(Continued)

(58) Field of Classification Search
CPC ............. A61B 17/1675; A61B 17/1764; A61F 2/30734; A61F 2/3859; A61F 2/461;
(Continued)

(56) References Cited

U.S. PATENT DOCUMENTS 3,924,274 A 12/1975 Heimke et al.
3,986,212 A 10/1976 Sauer
(Continued)

FOREIGN PATENT DOCUMENTS

DE 2842847 A1 4/1980
DE 102010044571 A1 3/2012
(Continued)

OTHER PUBLICATIONS

International Search Report and Written Opinion for Application No. PCT/US2012/068473 dated Mar. 8, 2013.
(Continued)

*Primary Examiner* — Bruce E Snow
(74) *Attorney, Agent, or Firm* — Lerner David LLP

(57) ABSTRACT

A distal femoral joint replacement system includes a femoral component having condylar articular surfaces, a stem extending from the femoral component, and a void filler for filling a bone void within a femur. The void filler includes a body and a plurality of legs extending from the body. The body has a sidewall defining an opening for receipt of the stem which extends along a length of the body and extends through the sidewall so as to form a side-slot in the sidewall that extends along an entire length of the sidewall. The plurality of legs each have a first end connected to the body and a second end remote from the body. The legs each have an outer surface that tapers between the first and second ends and is configured to register with a corresponding inner surface of a bone void when implanted in an end of the femur.

19 Claims, 19 Drawing Sheets

Related U.S. Application Data continuation of application No. 15/585,824, filed on May 3, 2017, now Pat. No. 10,524,806, which is a continuation of application No. 14/208,718, filed on Mar. 13, 2014, now Pat. No. 9,668,758.

(60) Provisional application No. 61/779,302, filed on Mar. 13, 2013.

(51) Int. Cl.
  *A61B 17/17* (2006.01)
  *A61F 2/30* (2006.01)
  *A61F 2/46* (2006.01)
  *A61B 90/00* (2016.01)

(52) U.S. Cl.
  CPC ...... *A61B 17/1764* (2013.01); *A61F 2/30724* (2013.01); *A61F 2/30734* (2013.01); *A61F 2/30767* (2013.01); *A61F 2/38* (2013.01); *A61F 2/3859* (2013.01); *A61F 2/461* (2013.01); *A61B 2090/036* (2016.02); *A61B 2090/062* (2016.02); *A61F 2002/3021* (2013.01); *A61F 2002/3069* (2013.01); *A61F 2002/3093* (2013.01); *A61F 2002/30332* (2013.01); *A61F 2002/30736* (2013.01)

(58) Field of Classification Search
  CPC .... A61F 2002/30332; A61F 2002/3069; A61F 2002/30736
  See application file for complete search history.

(56) References Cited

U.S. PATENT DOCUMENTS

| | | |
|---|---|---|
| 4,065,817 A | 1/1978 | Branemark et al. |
| 4,158,893 A | 6/1979 | Swanson |
| 4,306,550 A | 12/1981 | Forte |
| 4,341,206 A | 7/1982 | Perrett et al. |
| 4,463,444 A | 7/1984 | Daniels et al. |
| 4,549,319 A | 10/1985 | Meyer |
| 4,681,589 A | 7/1987 | Tronzo |
| 4,693,721 A | 9/1987 | Ducheyne |
| 4,714,471 A | 12/1987 | Grundei |
| 4,728,335 A | 3/1988 | Jurgutis |
| 4,735,625 A | 4/1988 | Davidson |
| 4,738,256 A | 4/1988 | Freeman et al. |
| 4,751,922 A | 6/1988 | DiPietropolo |
| 4,777,942 A | 10/1988 | Frey et al. |
| 4,790,852 A * | 12/1988 | Noiles ................. A61B 17/175 623/23.46 |
| 4,822,366 A | 4/1989 | Bolesky |
| 4,846,839 A | 7/1989 | Noiles |
| 4,944,757 A | 7/1990 | Martinez et al. |
| 4,997,448 A | 3/1991 | Filer |
| 5,011,496 A | 4/1991 | Forte et al. |
| 5,035,717 A | 7/1991 | Brooks |
| 5,047,033 A | 9/1991 | Fallin |
| 5,049,157 A | 9/1991 | Mittelmeier et al. |
| 5,061,287 A | 10/1991 | Feiler |
| 5,080,685 A | 1/1992 | Bolesky et al. |
| 5,108,398 A | 4/1992 | McQueen et al. |
| 5,122,134 A | 6/1992 | Borzone et al. |
| 5,152,797 A | 10/1992 | Luckman et al. |
| 5,190,548 A | 3/1993 | Davis |
| 5,192,283 A | 3/1993 | Ling et al. |
| 5,342,363 A | 8/1994 | Richelsoph |
| 5,342,366 A | 8/1994 | Whiteside et al. |
| 5,387,218 A | 2/1995 | Meswania |
| 5,403,320 A | 4/1995 | Luman et al. |
| 5,411,505 A | 5/1995 | Mumme |
| 5,445,642 A | 8/1995 | McNulty et al. |
| 5,480,453 A | 1/1996 | Burke |
| 5,489,311 A | 2/1996 | Cipolletti |
| 5,496,324 A | 3/1996 | Barnes |
| 5,527,316 A | 6/1996 | Stone et al. |
| 5,534,005 A | 7/1996 | Tokish, Jr. et al. |
| 5,540,694 A | 7/1996 | DeCarlo, Jr. et al. |
| 5,591,233 A | 1/1997 | Kelman et al. |
| 5,649,299 A | 7/1997 | Battin et al. |
| 5,755,720 A | 5/1998 | Mikhail |
| 5,755,793 A | 5/1998 | Smith et al. |
| 5,766,261 A | 6/1998 | Neal et al. |
| 5,782,921 A | 7/1998 | Colleran et al. |
| 5,824,097 A | 10/1998 | Gabriel et al. |
| 5,906,644 A | 5/1999 | Powell |
| 5,931,841 A | 8/1999 | Ralph |
| 5,951,603 A | 9/1999 | O'Neil et al. |
| 5,957,925 A | 9/1999 | Cook et al. |
| 5,976,145 A | 11/1999 | Kennefick, III |
| 5,976,147 A | 11/1999 | LaSalle et al. |
| 5,984,968 A | 11/1999 | Park |
| 5,989,257 A | 11/1999 | Tidwell et al. |
| 5,989,261 A | 11/1999 | Walker et al. |
| 5,993,455 A | 11/1999 | Noble |
| 6,010,534 A | 1/2000 | O'Neil et al. |
| 6,053,945 A | 4/2000 | O'Neil et al. |
| 6,071,311 A | 6/2000 | O'Neil et al. |
| 6,139,584 A | 10/2000 | Ochoa et al. |
| 6,152,963 A | 11/2000 | Noiles et al. |
| 6,171,342 B1 | 1/2001 | O'Neil et al. |
| 6,197,065 B1 | 3/2001 | Martin et al. |
| 6,214,052 B1 | 4/2001 | Burkinshaw |
| 6,214,053 B1 | 4/2001 | Ling et al. |
| 6,241,722 B1 | 6/2001 | Dobak et al. |
| 6,245,113 B1 | 6/2001 | Revie et al. |
| 6,440,171 B1 | 8/2002 | Doubler et al. |
| 6,494,913 B1 | 12/2002 | Huebner |
| 6,508,841 B2 | 1/2003 | Martin et al. |
| 6,702,822 B1 | 3/2004 | Noiles et al. |
| 6,712,855 B2 | 3/2004 | Martin et al. |
| 6,887,276 B2 | 5/2005 | Gerbec et al. |
| 6,902,583 B2 | 6/2005 | Gerbec et al. |
| 6,945,556 B2 | 9/2005 | Maertens |
| 7,074,224 B2 | 7/2006 | Daniels et al. |
| 7,090,677 B2 | 8/2006 | Fallin et al. |
| 7,141,073 B2 | 11/2006 | May et al. |
| 7,255,702 B2 | 8/2007 | Serra et al. |
| 7,291,174 B2 | 11/2007 | German et al. |
| 7,297,163 B2 | 11/2007 | Huebner |
| 7,393,355 B2 | 7/2008 | Tulkis et al. |
| 7,476,254 B2 | 1/2009 | White et al. |
| 7,481,814 B1 | 1/2009 | Metzger |
| 7,481,841 B2 | 1/2009 | Hazebrouck et al. |
| 7,537,664 B2 | 5/2009 | O'Neill et al. |
| 7,632,273 B2 | 12/2009 | Schnieders et al. |
| 7,670,383 B1 | 3/2010 | Brown et al. |
| 7,722,678 B2 | 5/2010 | Brown et al. |
| 7,785,328 B2 | 8/2010 | Christie et al. |
| 7,799,085 B2 | 9/2010 | Goodfried et al. |
| 7,806,936 B2 | 10/2010 | Wright |
| 7,832,405 B1 | 11/2010 | Schlueter et al. |
| 7,892,288 B2 | 2/2011 | Blaylock et al. |
| 7,892,290 B2 | 2/2011 | Bergin et al. |
| 7,918,892 B2 | 4/2011 | Huebner |
| 7,942,879 B2 | 5/2011 | Christie et al. |
| 8,029,573 B2 | 10/2011 | Podolsky |
| 8,048,166 B2 | 11/2011 | Brown et al. |
| 8,052,687 B2 | 11/2011 | Sackett et al. |
| 8,105,385 B2 | 1/2012 | Maroney et al. |
| 8,147,498 B2 | 4/2012 | Schlueter et al. |
| 8,147,861 B2 | 4/2012 | Jones et al. |
| 8,157,869 B2 | 4/2012 | Metzger et al. |
| 8,167,882 B2 | 5/2012 | Sackett et al. |
| 8,177,788 B2 | 5/2012 | McLean et al. |
| 8,177,849 B2 | 5/2012 | Meyers et al. |
| 8,187,336 B2 | 5/2012 | Jamali |
| 8,273,091 B2 | 9/2012 | Elghazaly |
| 8,337,498 B2 | 12/2012 | Rasmussen |
| 8,350,186 B2 | 1/2013 | Jones et al. |
| 8,372,157 B2 | 2/2013 | Petersen et al. |
| 8,382,849 B2 | 2/2013 | Thomas |
| 8,424,183 B2 | 4/2013 | Thomas |
| 8,444,699 B2 | 5/2013 | Metzger et al. |

(56) References Cited

U.S. PATENT DOCUMENTS

| | | |
|---|---|---|
| 8,506,645 B2 | 8/2013 | Blaylock et al. |
| 8,535,385 B2 | 9/2013 | Hanssen et al. |
| 8,585,770 B2 | 11/2013 | Meridew et al. |
| 8,696,757 B2 | 4/2014 | Brown et al. |
| 8,728,387 B2 | 5/2014 | Jones et al. |
| 8,790,402 B2 | 7/2014 | Monaghan et al. |
| 9,011,444 B2 | 4/2015 | Primiano et al. |
| 9,149,282 B2 | 10/2015 | Servidio et al. |
| 9,259,257 B2 | 2/2016 | Bagga et al. |
| 9,345,523 B2 | 5/2016 | Segina et al. |
| 9,526,513 B2 | 12/2016 | Collazo et al. |
| 9,668,758 B2 | 6/2017 | Collazo et al. |
| RE47,149 E | 12/2018 | Primiano et al. |
| 10,149,763 B2 | 12/2018 | Krebs et al. |
| 10,265,083 B2 * | 4/2019 | Servidio ............ A61B 17/1662 |
| 10,299,929 B2 | 5/2019 | Collazo |
| 10,335,171 B2 | 7/2019 | Collazo et al. |
| RE48,163 E | 8/2020 | Primiano et al. |
| 11,172,941 B2 | 11/2021 | Collazo et al. |
| 11,173,034 B2 | 11/2021 | Collazo |
| 2001/0009974 A1 | 7/2001 | Reisfeld |
| 2003/0171756 A1 | 9/2003 | Fallin et al. |
| 2003/0171815 A1 | 9/2003 | Kana et al. |
| 2004/0049285 A1 | 3/2004 | Haas |
| 2004/0092951 A1 | 5/2004 | Serra et al. |
| 2004/0162619 A1 | 8/2004 | Blaylock et al. |
| 2005/0288676 A1 | 12/2005 | Schnieders et al. |
| 2006/0147332 A1 | 7/2006 | Jones et al. |
| 2006/0241776 A1 | 10/2006 | Brown et al. |
| 2007/0088443 A1 | 4/2007 | Hanssen et al. |
| 2007/0118229 A1 | 5/2007 | Bergin et al. |
| 2007/0142914 A1 | 6/2007 | Jones et al. |
| 2007/0162033 A1 | 7/2007 | Daniels et al. |
| 2008/0147071 A1 | 6/2008 | Serra et al. |
| 2008/0161812 A1 | 7/2008 | Sackett et al. |
| 2008/0306600 A1 | 12/2008 | Huebner |
| 2009/0157190 A1 | 6/2009 | Collazo et al. |
| 2010/0057212 A1 | 3/2010 | Thomas |
| 2010/0076565 A1 * | 3/2010 | Thomas ............ A61F 2/30734 606/86 R |
| 2010/0082031 A1 | 4/2010 | Sackett et al. |
| 2010/0114323 A1 | 5/2010 | Deruntz et al. |
| 2010/0222891 A1 | 9/2010 | Goodfried et al. |
| 2010/0286696 A1 | 11/2010 | Christie et al. |
| 2011/0009974 A1 | 1/2011 | Blaylock et al. |
| 2011/0015634 A1 | 1/2011 | Smith et al. |
| 2011/0190899 A1 | 8/2011 | Pierce et al. |
| 2012/0016482 A1 | 1/2012 | Mooradian et al. |
| 2012/0035733 A1 | 2/2012 | Porter et al. |
| 2012/0089146 A1 | 4/2012 | Ferko et al. |
| 2012/0209270 A1 | 8/2012 | Segina et al. |
| 2012/0226281 A1 | 9/2012 | Sackett et al. |
| 2013/0053976 A1 | 2/2013 | Gugler et al. |
| 2013/0150858 A1 | 6/2013 | Primiano et al. |
| 2013/0172892 A1 | 7/2013 | Servidio et al. |
| 2013/0211536 A1 | 8/2013 | Metzger et al. |
| 2013/0264749 A1 | 10/2013 | Jones et al. |
| 2013/0268085 A1 | 10/2013 | Dong et al. |
| 2014/0276882 A1 | 9/2014 | Collazo et al. |
| 2014/0277528 A1 | 9/2014 | Mines et al. |
| 2014/0277567 A1 | 9/2014 | Collazo et al. |
| 2015/0105779 A1 | 4/2015 | Smith et al. |
| 2015/0190150 A1 | 7/2015 | Primiano et al. |
| 2015/0282935 A1 | 10/2015 | Kuldjanov et al. |
| 2015/0366567 A1 | 12/2015 | Servidio et al. |
| 2023/0233328 A1 * | 7/2023 | Cullum ................ A61F 2/3662 623/18.11 |

FOREIGN PATENT DOCUMENTS

| | | |
|---|---|---|
| EP | 0016480 A1 | 10/1980 |
| EP | 1570812 A1 | 9/2005 |
| EP | 2168506 A1 | 3/2010 |
| EP | 2168586 A1 | 3/2010 |
| EP | 2181672 A1 | 5/2010 |
| GB | 2159416 A | 12/1985 |
| WO | 03094698 A2 | 11/2003 |
| WO | 2006127486 A2 | 11/2006 |
| WO | 2008069800 A1 | 6/2008 |
| WO | 2009094698 A1 | 8/2009 |

OTHER PUBLICATIONS

Partial International Search Report dated Mar. 15, 2013 for Application No. PCT/US2012/072087.

Jones et al., U.S. Appl. No. 13/441,154, filed Apr. 6, 2012, titled "Surface Modified Unit Cell Lattice Structures for Optimized Secure Freeform Fabrication".

International Search Report and Written Opinion for Application No. PCT/US2012/072087 dated May 2, 2013.

Schreurs, et al., Femoral Component Revision with Use of Impaction Bone-Grafting and a Cemented Polished Stem. Surgical Technique, The Journal of Bone & Joint Surgery, Sep. 2006, pp. 259-274.

Lonner, et al., Impaction Grafting and Wire Mesh for Uncontained Defects in Revision Knee Arthroplasty, Clinical Orthopaedics and Related Research, No. 404, pp. 145-151, Copyright Nov. 2002, Lippincott Williams & Wilkins, Inc.

Stryker Howmedica Osteonics, X-change Revision Instruments System, Copyright Howmedica Osteonics, Sep. 2001.

Knee Revision Product Portfolio, DePuy International Ltd., a Johnson & Johnson Company, Cat. No: 9075-40-000 version 1, Copyright 2009.

Zimmer, Trabecular Metal, Tibial and Femoral Cones Surgical Techniques, Copyright 2011.

Extended European Search Report for Application No. EP14159399 dated Jun. 6, 2014.

Extended European Search Report with Written Opinion for U.S. Appl. No. 20/173,076 dated Aug. 12, 2020, 6 pages.

McQueen, Wichita Fusion Nail Surgical Technique, Oct. 2006, 12 pages, Stryker.

Depuy, S-ROM Noiles Rotating Hinge, Surgical Technique and Reference Guide, 2002, 44 pages.

* cited by examiner

VOID FILLING JOINT PROSTHESIS AND ASSOCIATED INSTRUMENTS

CROSS-REFERENCE TO RELATED APPLICATIONS

This application is a continuation of U.S. application Ser. No. 16/694,113, filed Nov. 25, 2019, which is a continuation of U.S. application Ser. No. 15/585,824, filed May 3, 2017, now U.S. Pat. No. 10,524,806, which is a continuation of U.S. application Ser. No. 14/208,718, filed Mar. 13, 2014, now U.S. Pat. No. 9,668,758, which claims the benefit of the filing date of U.S. Provisional Patent Application No. 61/779,302, filed Mar. 13, 2013, the disclosures of which are hereby incorporated herein by reference.

BACKGROUND OF THE INVENTION

Joint replacement surgery is a common orthopedic procedure for joints such as the shoulder, hip, knee, ankle and wrist. Prior to implanting prosthetic components in a joint of a patient, a surgeon generally has to resect at least a portion of the patient's native bone in order to create a surface and/or recess or void for supporting, accepting or receiving at least a portion of the prosthetic components being implanted. Generally, a surgeon only resects the amount of bone that is needed in order to properly implant the prosthetic components in the joint because once native bone is resected from a joint, it is gone forever. Thus, the surgeon typically attempts to maintain as much of the native structural integrity of the joint as he or she can during the resection process.

When previously implanted prosthetic components fail for any one of a variety of reasons, a revision procedure is often necessary. An issue generally encountered by surgeons replacing joints during a revision procedure is the additional loss of native bone near the joint being replaced. This bone loss is typically due to movement of the component or components after implantation or even degeneration or further degeneration of the bone, which can form bone voids that have unpredictable and non-uniform shapes. In addition, revision procedures often involve the removal of additional bone, which makes maintaining or otherwise restoring the structural integrity often afforded by native bone of great importance.

For instance, when bone voids are observed in either the proximal tibia or distal femur, or both, it is standard surgical practice to fill those voids as part of the revision surgical procedure. The preferred practice is to fill those voids with weight bearing void fillers, typically made of an implant-grade metal such as titanium. However, because the bone voids are typically irregular in shape, some preparation of the bone void area is typically required prior to implantation of the void filler. This preparation (typically by reaming, broaching or milling) ensures there is sufficient room in the bone void for the void filler. An accurate fit between the shaped bone void and the void filler is also important for establishing joint line, and allowing for weight bearing and bone remodeling during the recovery process. Of course, this procedure involves the removal of even more native bone, so great lengths should be taken to minimize the overall amount removed.

Different methods are commonly used to attempt to prepare the bone void area to create an accurate fit between the shaped bone void and void filler. One method is to ream along the intramedullary ("IM") axis, followed by broaching. Another method is to ream along the IM axis, followed by freehand burring or rongeur bone removal, which may also be followed by broaching. Problems with these methods include that reaming is performed on the IM axis only, so that void areas at a distance from the IM axis, which commonly occur, can only be resected using manual methods. Moreover, broaching generally has at least two problems. First, a manual operation can be time consuming, particularly in cases of sclerotic bone, which exposes the patient to an increased risk of infection and longer recovery. Second, in the case of large bone voids, broaching generally needs to be performed in a multi-step process because attempting to remove high volumes of bone in a single broaching step generally requires high impact forces to the bone. Also, freehand bone removal, either powered or unpowered, such as with a burr or rongeur, often does not produce accurate void shapes to receive predefined prosthetic components. A typical result is that areas remain where the outer walls of the void filler do not contact the void, which may lead to undesirable stress distribution and possible loss of bone regrowth. Also typical is the time consuming requirement of iterative bone removal, with multiple checks against the void fillers, to obtain a correct fit.

Occasionally the bone loss or bone deformity is so significant that the surgeon must resect a portion of bone along its length and supplement the bone loss with a bone augment. Since the surgeon typically attempts to preserve as much native bone as possible, the result of the resection is typically a bone that has multilevel plateaus, where the bone augment is commonly placed between the joint prosthesis and one plateau in order to augment the missing bone, and the prosthesis itself is placed against the other plateau. However, this resection generally does not eliminate the need for a void filler. Generally, the bone void extends through the multilevel plateaus, which creates an area where the void filler would be exposed and would interfere with the placement of the bone augment when implanted. Unfortunately, this situation is often unpredictable as the surgeon is often unaware of the need to augment until the previous prosthesis has been removed.

Thus, there is a need for a bone void filler that is adaptable to be used in both a joint revision procedure requiring a bone augment so as to not interfere with the placement of the augment and a joint revision procedure where a bone augment is not needed.

BRIEF SUMMARY OF THE INVENTION

In one aspect of the present disclosure, a bone void filling prosthesis includes a body having a frustoconical profile, a length defined between a first end and a second end, and an aperture extending through the entirety of the length. The aperture defines a sidewall having a thickness spanning between an outer surface and an inner surface of the body. The void filling prosthesis also has at least one leg having a frustoconical profile, and a first and second end. The at least one leg is coupled to and extends away from the body such that the first end of the at least one leg is disposed between the first and second ends of the body.

Additionally, the at least one leg may have a first surface and a second surface. The first surface may be disposed at the second end of the at least one leg. The first surface may intersect the second surface at an angle, and the angle may be substantially equal to an angle formed between two resected surfaces of a femur bone. Further, the at least one leg may include a bone contact surface and a prosthesis facing surface. The bone contact surface may be formed from a porous material and the prosthesis facing surface being formed from a solid material. The bone contact surface may intersect the prosthesis facing surface at a prosthesis boundary. The prosthesis boundary may be formed of a solid material such as to form a rim of solid material along the bone contact surface.

Continuing with this aspect, the at least one leg may include a first leg and a second leg coupled to the body. The first leg and second leg may each have a frustoconical profile. Further, the first leg may be separated from the second leg by a space. The space may define a first inner surface extending along the first leg and a second inner surface extending along the second leg. The first inner surface may have a planar portion and a stepped portion.

Also, the aperture may extend through the thickness of the sidewall from the first end to the second end of the body and may further define a curved portion and a first and second wall portions. The curved portion may have a frustoconical outer surface and a cylindrical inner surface. The curved portion may have an inner radius and the first and second wall portions may each have a planar inner surface. The first and second wall portions may be coupled to the curved portion such that the planar inner surfaces of the first and second wall portions are tangent to an imaginary cylinder defined by the curved portion. Alternatively, where the inner surface of the curved portion is frustoconical, the first and second wall portions may be coupled to the curved portion such that the planar inner surfaces of the first and second wall portions are tangent to an imaginary conical frustrum defined by the curved portion.

In another aspect of the present disclosure, a bone void filling prosthesis includes a body having a length defined between a first end and a second end, and an aperture extending through the entirety of the length. The aperture defines a sidewall having a thickness spanning between an outer surface and an inner surface of the body. The aperture extends through the sidewall from the first end to the second end.

Additionally, the aperture may define a curved portion and a first and second wall portions. The first and second wall portions may be separated by a distance. The curved portion may have a frustoconical outer surface and a cylindrical inner surface. Further, the curved portion may have an inner radius and the first and second wall portions may each have a planar inner surface. In one embodiment, the first and second wall portions may be coupled to the curved portion such that the planar inner surfaces of the first and second wall portions are tangent to an imaginary cylinder defined by the curved portion. Alternatively, the first and second wall portions may be coupled to the curved portion such that the planar inner surfaces of the first and second wall portions are tangent to an imaginary conical frustrum defined by the curved portion.

Continuing with this aspect, the bone void filling prosthesis may also include at least one leg having a first end and second end. The at least one leg may be coupled to and extend away from the body. The body and the at least one leg may each have a frustoconical profile.

In a further aspect of the present disclosure, a bone void filling prosthesis includes a body having a length defined between a first end and a second end, and an aperture extending through the entirety of the length. The aperture defines a sidewall having a thickness spanning between an outer surface and an inner surface of the body. The outer surface is formed of a porous material for promoting bony ingrowth, and the inner surface is formed of solid material. The inner surface and outer surface are connected at a boundary of the prosthesis by a rim formed of solid material that extends through the entirety of the thickness and forms at least a portion of the outer surface. The rim may include a channel extending therein for receipt of an adhesive.

In yet another aspect of the present disclosure, a joint replacement system includes a void filling prosthesis having a body. The body includes a length defined between a first end and a second end and an aperture extending through the entirety of the length. The aperture defines a sidewall having a thickness spanning between an outer surface and an inner surface of the body. The aperture extends through the thickness of the sidewall at one location throughout the entire length of the body and further defines a curved portion and a first and second wall portions. The curved portion has a radius and the first and second wall portions are separated by a distance. The system also includes a stem component having a cross-sectional thickness smaller than the radius of the curved portion and the distance between the first and second wall portions so as to leave about at least a 2 mm gap between the stem component and inner surface of body when the stem component is inserted into the aperture of the body.

Additionally, the first wall portion may define a plane tangent to an imaginary circle defined by the curved portion. The curved portion of the body may have an outer surface having a frustoconical taper from the first end to the second end of the body.

The system may also include a reamer assembly that includes an intramedullary component, a support, and a reamer. The curved portion of the body may include an outer surface having a frustoconical taper from the first end to the second end of the body. The reamer may include a shaft and a frustoconical head having a taper from a first end to a second end of the head. The taper may be substantially equal to the frustoconical taper of the outer surface of the curved portion.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1:
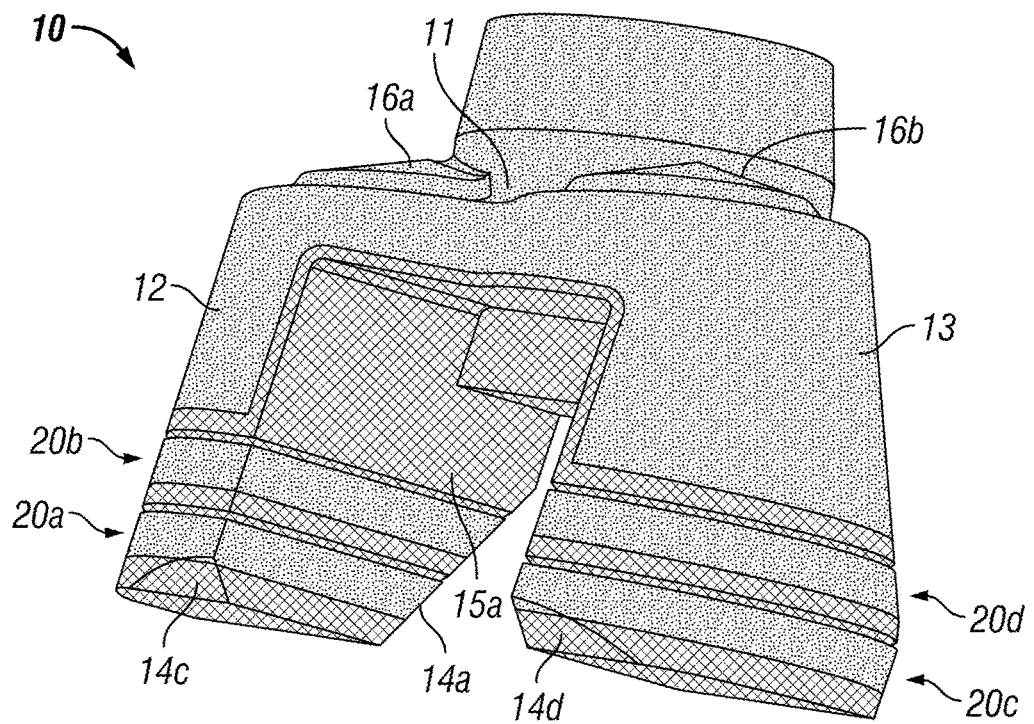
FIG. 1 shows a perspective view of one embodiment of a void filling prosthesis.
Figure 2:
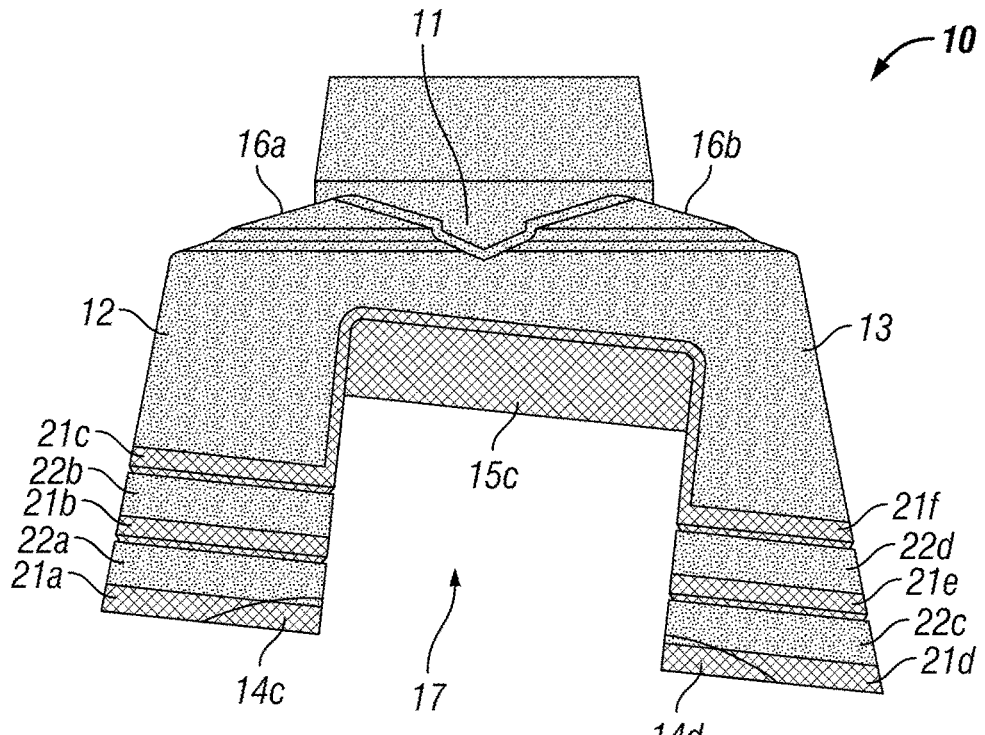
FIG. 2 shows a front view of the void filling prosthesis of FIG. 1.
Figure 3:
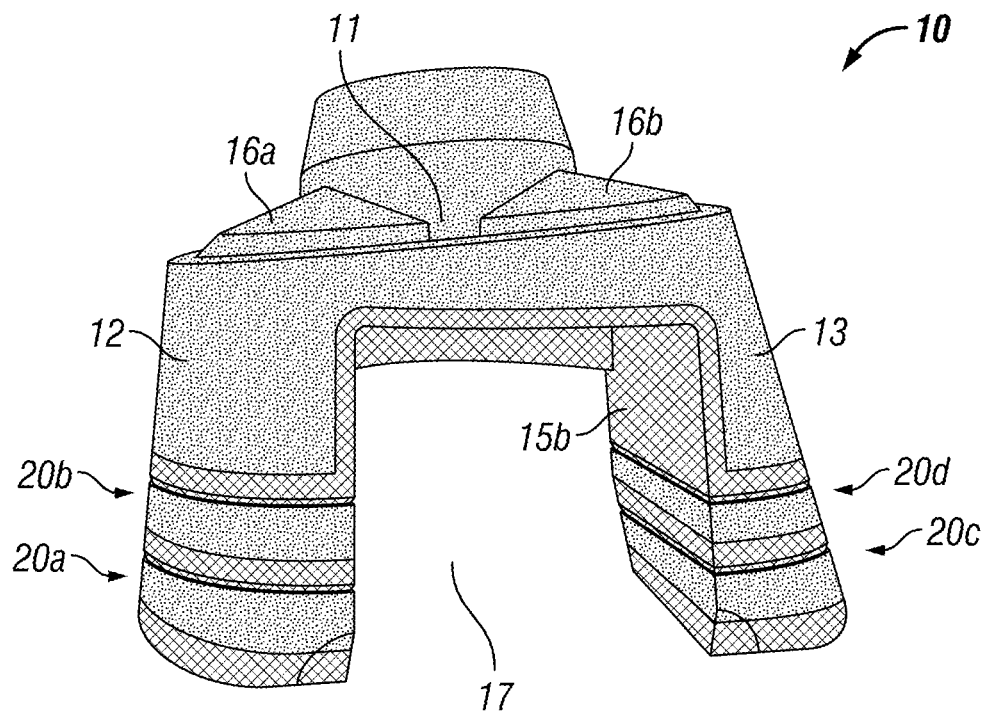
FIG. 3 shows another perspective view of the void filling prosthesis of FIG. 1.
Figure 4:
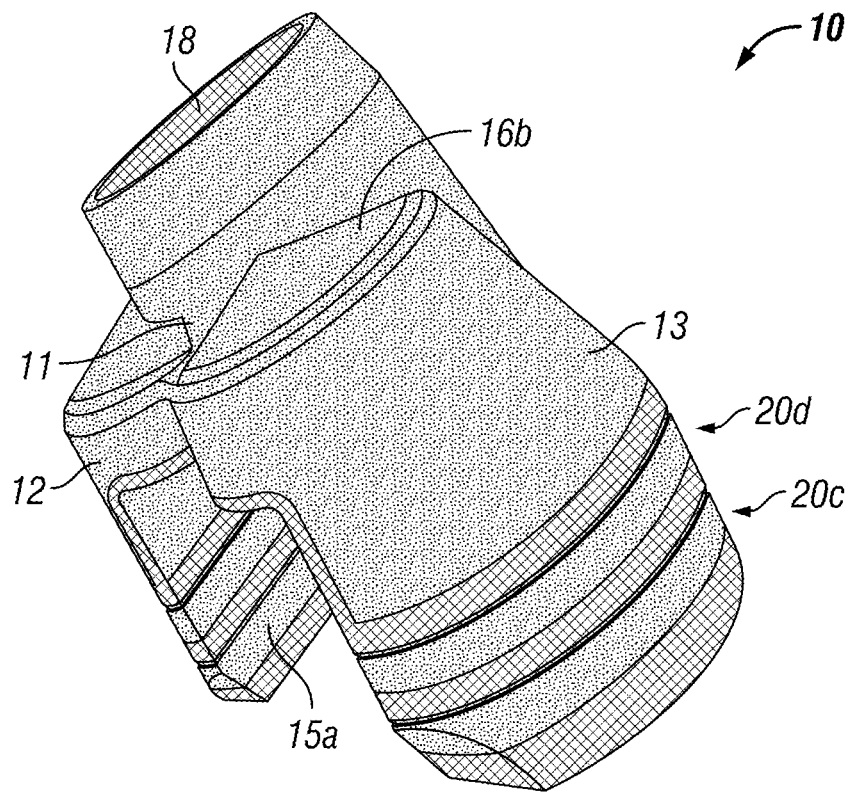
FIG. 4 shows a side perspective view of the void filling prosthesis of FIG. 1.

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face and the term "posterior" means toward the back of the body. The term "medial" means toward the midline of the body and the term "lateral" means away from the midline of the body. Also, as used herein, the terms "about," "generally" and "substantially" are intended to mean that slight deviations from absolute are included within the scope of the term so modified.

FIGS. 1-4 depict a first embodiment of a void filling prosthesis 10. The void filling prosthesis 10 includes a central body 11, a medial leg 13, and a lateral leg 12. In another embodiment, the void filling prosthesis 10 may include a central body and only a medial leg 13 or lateral leg 12. The central body 11 is generally cylindrical. However, this cylindrical shape may take the form of a portion that has a constant diameter and a portion that is slightly tapered such that it is generally frustoconical. The central body 11 includes an aperture 18 that extends through the central body 11 in order to allow the passage of an IM stem of a femoral component 30. This aperture 18 forms a wall 19, which is integrated with the lateral and medial legs 12, 13 forming a monolithic structure.

The lateral and medial legs 12, 13 may be offset posteriorly from a median transverse axis of the central body 11. Further, the lateral and medial legs 12, 13 may be located in close proximity, but may be separated generally by a space 17 that penetrates through both legs and forms a saddle-like structure in order to provide clearance for a femoral cam box 33 of a femoral component 30. This space 17 forms inner surfaces 15a-d that abut the femoral cam box 33 when implanted. These inner surfaces 15a-d may be flat, planar walls, or they may be stepped to provide surfaces conducive for bonding with bone cement. Further, inner surface 15d may be obliquely angled with respect to the longitudinal axis of the central body 11 in order to account for the angle of the IM stem (not shown) with respect to the cam box.

Further geometric features may be incorporated into the medial and lateral legs 12, 13 in order to provide clearance for the structure of the femoral component 30. For instance, inclined surfaces 14a-d may be fashioned into each leg in order to provide clearance for a bone interface surface 35 of the femoral component 30.

The remainder of the lateral and medial legs 12, 13 that has not been shaped to form clearance space is depicted as having a generally frustoconical profile. This geometric profile is preferred in order to conform more closely to bone voids created by the reaming instrumentation. However, this is merely an example of a geometry that the medial and lateral legs 12, 13 may form. The legs 12, 13 may have other geometries, such as box-like geometries. Further, the medial and lateral legs 12, 13 may be symmetric with respect to one another, or they may be asymmetric where one leg 12, 13 may be larger than the other 12, 13 and/or one leg 12, 13 may have a different geometry. A conical structure 16a-b may be disposed at one end of each of the lateral and medial legs 12, 13. This conical structure 16a-b may help prevent rotation of the prosthesis 10 when implanted in the bone and help the prosthesis 10 settle into the proper orientation and more closely conform to the void formed by the reaming instruments.

Referring to FIGS. 1-4 and 7-8, each leg 12, 13 is shown to include two removable portions 20a-d at an end of each leg 12, 13. While two removable portions 20a-d are shown, this is merely an example. Each leg 12, 13 may include any number of selectively removable portions 20a-d, including just one. Alternatively, one leg 12, 13 may include at least one selectively removable portion 20a-d while the other leg 12, 13 may have no selectively removable portions 20a-d. Where one or more selectively removable portions 20a-d is removed from a leg 12, 13, the length of the leg 12, 13 is decreased in order to make room in the joint cavity for a bone augment, for example. This removability provides the operator the operating room capability and flexibility to configure the void filling device 10 to work in conjunction with a bone augment, or alternatively work where no augment is needed. Thus, each selectively removable portion 20a-d is shaped to conform to the geometries of the void filling prosthesis 10 as though they will never be removed. Further, where these portions 20a-d are not removed, they provide structural support to the prosthesis 10.

Where there are multiple selectively removable portions 20a-d, they are layered along the length of each leg 12, 13 as far as needed to accommodate a bone augment. Each selectively removable portion 20a-d may have a first section 22a-d made from a weaker material and a second section 21a-f made from a stronger material, where the two sections 21a-f, 22a-d are layered along the length of each leg 12, 13.

In a preferred embodiment, the weaker and stronger material may be made from the same metallic material, but the weaker material may have a higher porosity than that of the stronger material allowing for a seamless transition between these two sections 21a-f, 22a-d, but providing a region for easy separation. Separation is made easier by the fact that the more porous material is easier to separate and that the two sections 21a-f, 22a-d are visually recognizable indicating the separation location.

In one embodiment, the separation location may be designated by a small chamfer to receive a cutting blade between the first section 22a-d of one selectively removable portion 20a-d and the second section 21a-f of another selectively removable portion 20a-d. An example of the porous metallic material may be titanium, titanium alloy, stainless steel, cobalt chrome alloys, tantalum or niobium formed by Selective Laser Melting ("SLM") as described in U.S. Pat. No. 7,537,664 titled "Laser-Produced Porous Surface," the entirety of which is incorporated-by-reference herein fully set forth herein and which is assigned to the same entity as the present invention. Additional examples are disclosed in U.S. application Ser. No. 11/027,421, filed Dec. 30, 2004, Ser. No. 11/295,008, filed Dec. 6, 2005, and Ser. No. 13/441,154, filed Apr. 6, 2012, and U.S. Pat. Nos. 8,350,186 and 8,147,861, the entireties of which are incorporated-by-reference herein as if fully set forth herein.

In an alternative embodiment, the weaker material may have the same porosity as the stronger material, but may be constructed from a material that has a lower modulus than the stronger material. In another embodiment, the entire void filling prosthesis 10 may be constructed from a porous metallic material including the selectively removable portions 20a-d with little or no variations in the porosity, but that the selectively removable portions 20a-d have score marks to designate the cutting points. In a further embodiment, the first section 22a-d may have an outer shell that is the same porosity as the remainder of the void filling prosthesis 10, and an interior portion constructed from the weaker material.

These selectively removable portions 20a-d may be removed by cutting along the weaker section 22a-d generally parallel and adjacent the stronger section 21a-f of another selectively removable portion 20b, 20d that is more proximate the central body using a cutting device. For instance a cutting device may be a guillotine-like device, an example of which is disclosed in U.S. application Ser. No. 12/002,002, filed Dec. 13, 2007, the entirety of which is incorporate-by-reference herein as if fully set forth herein. Where the selectively removable portion 20b, 20d is the last selectively removable portion along the length of that particular leg 12, 13, the leg 12, 13 may have a layer of stronger material 21c, 21f just adjacent to the weaker section 22b, 22d of that selectively removable portion 20b, 20d to facilitate removal.

The remainder of the void filling prosthesis 10 may also be partially constructed from porous metallic material as described above. In one embodiment, the surfaces in contact with the femoral component 30, such as internal surfaces 15a-d, may be constructed of solid metallic material, such as titanium as an example, while the remainder of the void filling prosthesis 10 may be constructed of porous metallic material.

Figure 5:
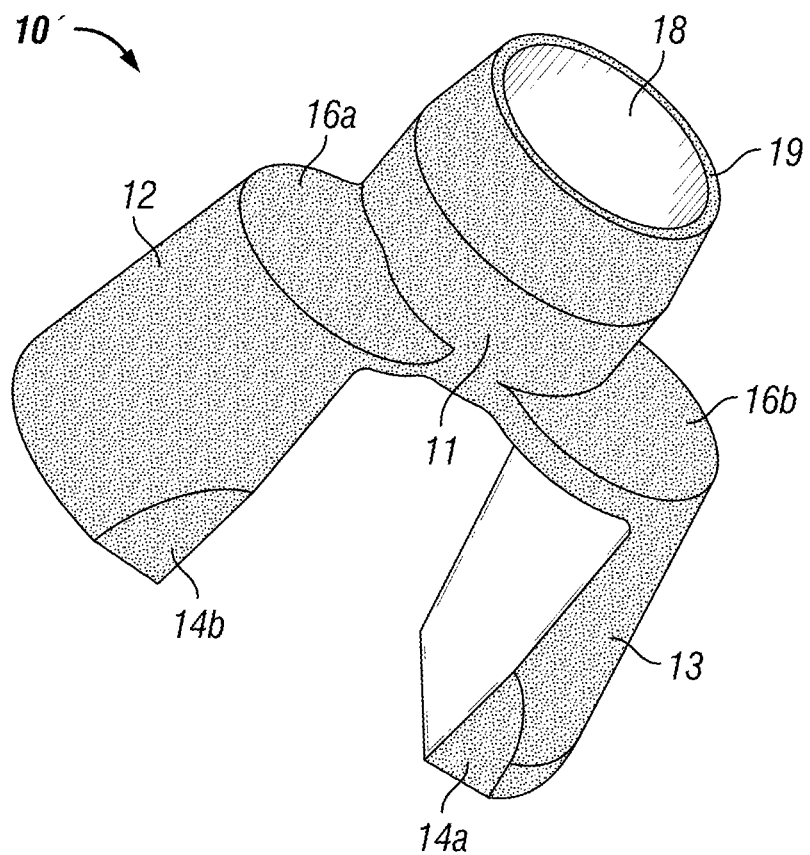
FIG. 5 shows a top perspective view of another embodiment of a void filling prosthesis of FIG. 1.
Figure 6:
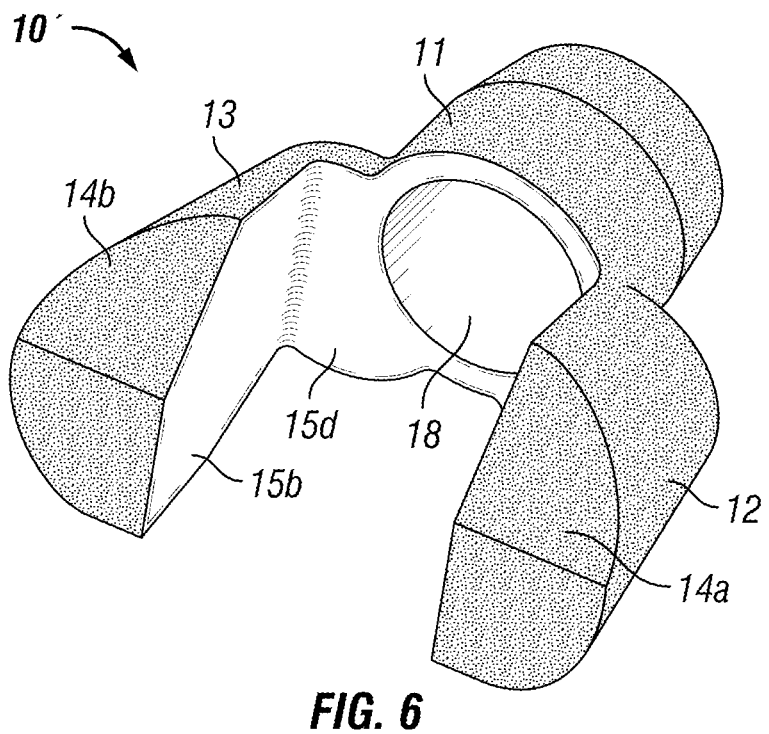
FIG. 6 shows a bottom perspective view of the void filling prosthesis of FIG. 5.
Figure 7:
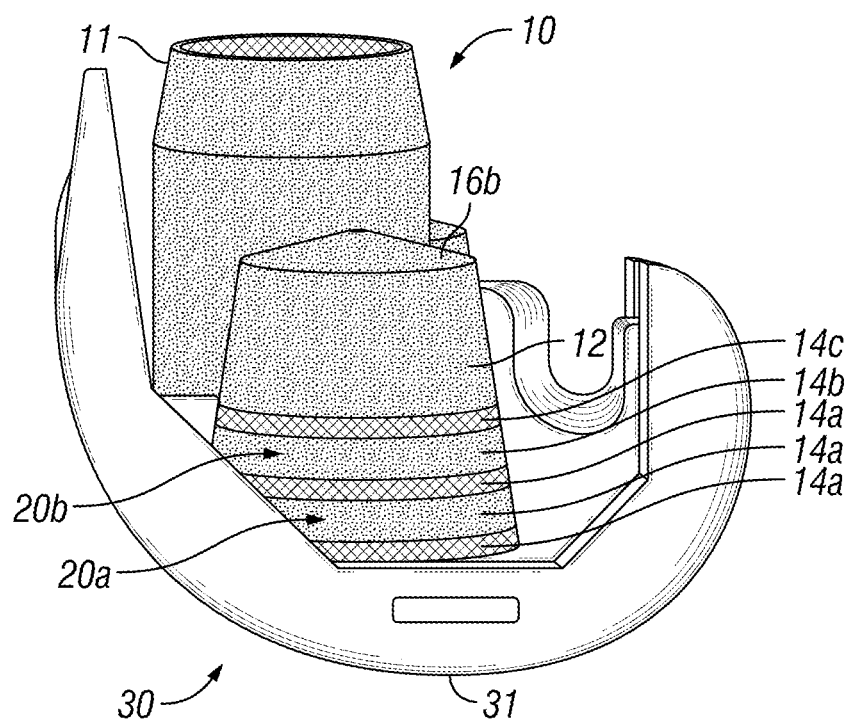
FIG. 7 shows a side view of the void filling prosthesis of FIG. 1 interfacing with a femoral component.
Figure 8:
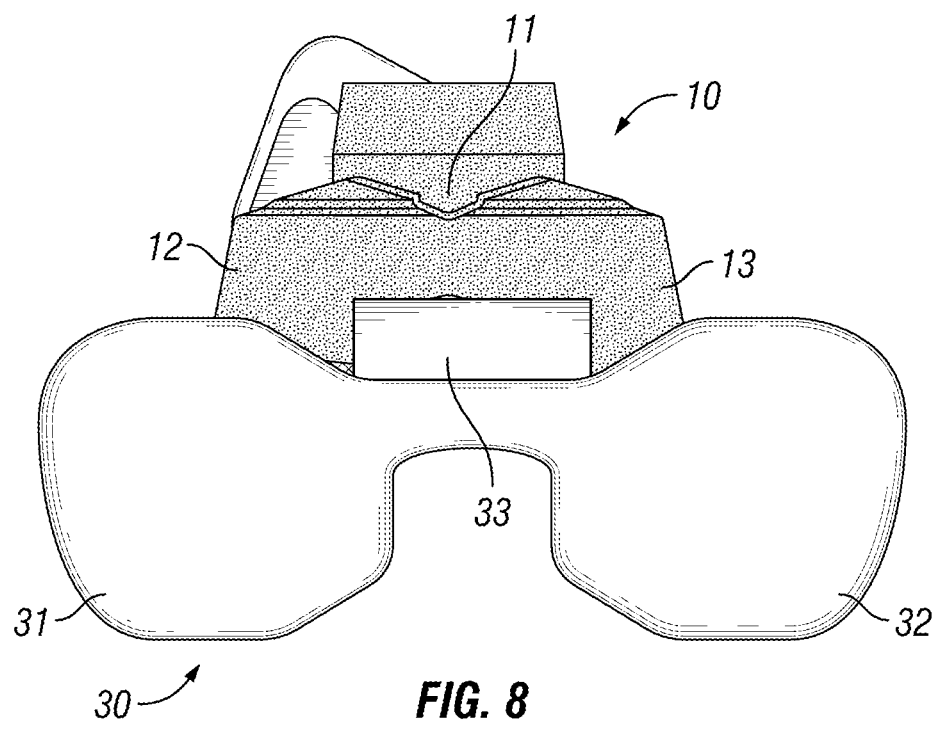
FIG. 8 shows a rear view of the void filling prosthesis of FIG. 1 interfacing with a femoral component.
Figure 9:
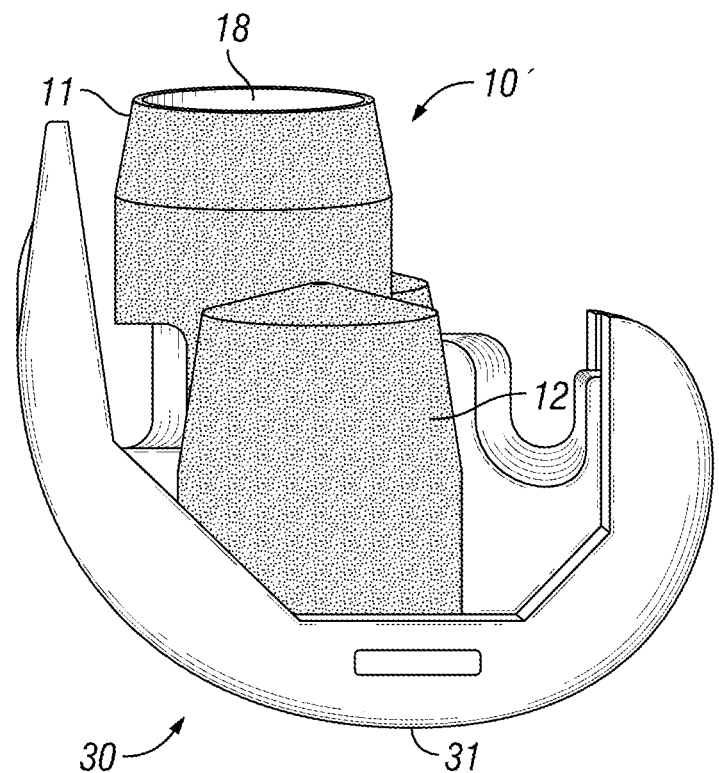
FIG. 9 shows a side view of the void filling prosthesis of FIG. 5 interfacing with a femoral component.
Figure 10:
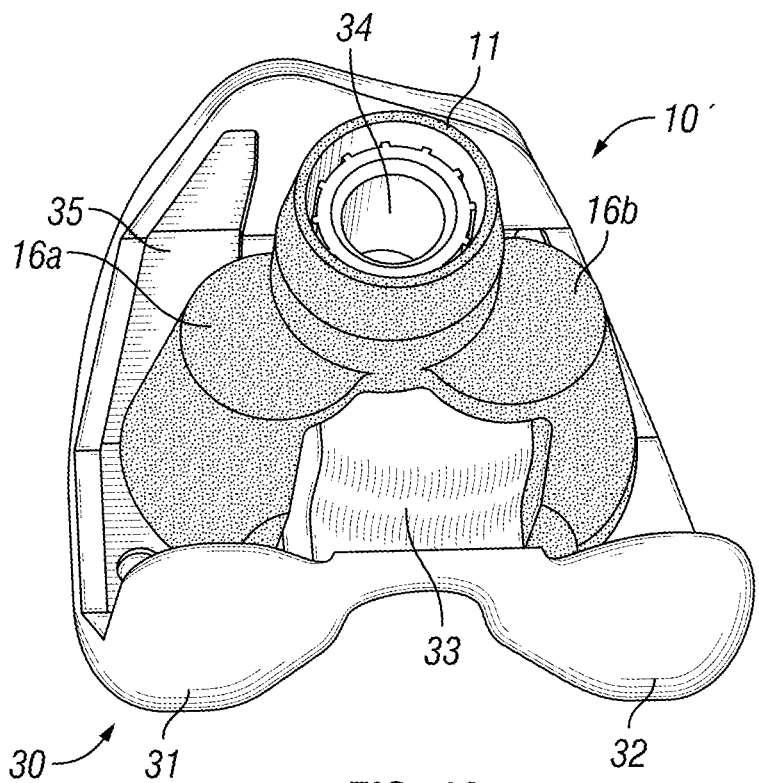
FIG. 10 shows a top perspective view of the void filling prosthesis of FIG. 5 interfacing with a femoral component.

FIGS. 5 and 6 depict an alternative embodiment wherein the bone void filler 10' does not include selectively removable portions 20a-d, but has substantially the same geometries as prosthesis 10. This embodiment may also be constructed from the same materials as that of prosthesis 10, including portions of porous metallic material. Further, this embodiment may also be constructed from solid metal or high strength polymeric material.

FIGS. 7-10 depict the interface between the void filling prosthesis 10, 10' and a femoral component 30. The femoral component 30 may be any femoral component 30, for example a femoral component 30 utilized in a posterior stabilized or total stabilized total knee prosthesis, for example the Scorpio® TS femoral component (Howmedica Osteonics, Mahwah, NJ).

The void filling prosthesis 10, 10' may be placed in contact with the femoral component such that aperture 18 of the central body 11 is placed over a stem portion of the femoral component 30 and the inner surfaces 15a-d are placed in contact with the cam box 33. In one embodiment, bone cement is placed between the inner surfaces 15a-d and the cam box 33 to provide for additional support. Such inner surfaces 15a-d may be stepped to provide more surface area for bonding to the cement.

In one embodiment, the distal ends of the legs 12, 13 do not contact the bone contacting surface 35 of the femoral component in order to provide some space for bone cement to flow and to provide space so that the operator can make minor corrections to the rotation of the femoral component 30.

A set of guided instruments may be provided to form the bone void to receive the void filling prosthesis. Included in this set of instruments may be an IM reamer 40, a boss reamer 50, a reamer guide assembly 60, an alignment handle 90, an alignment pin 100, a lobe reamer assembly 110, and a lobe trial 120.

Figure 11:
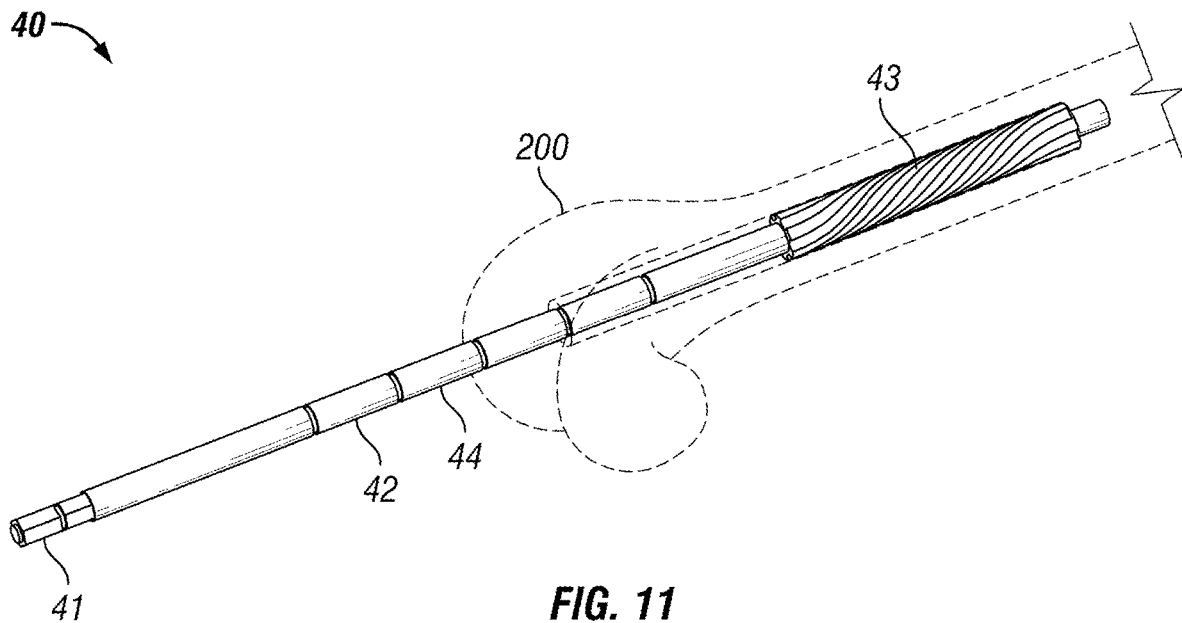
FIGS. 11-19 show a method and instrumentation for forming a bone void to receive the prostheses of FIG. 1 and FIG. 5.

The IM reamer 40, as depicted in FIG. 11, may include a shaft 42 that includes a plurality of depth indicators 44 situated along the length of the shaft 42 at designated intervals, and a reamer head 43 disposed at one end of the shaft. The other end of the shaft 41 may be configured to interface with a torque applying device, such as the chuck of a drill.

Figure 12:
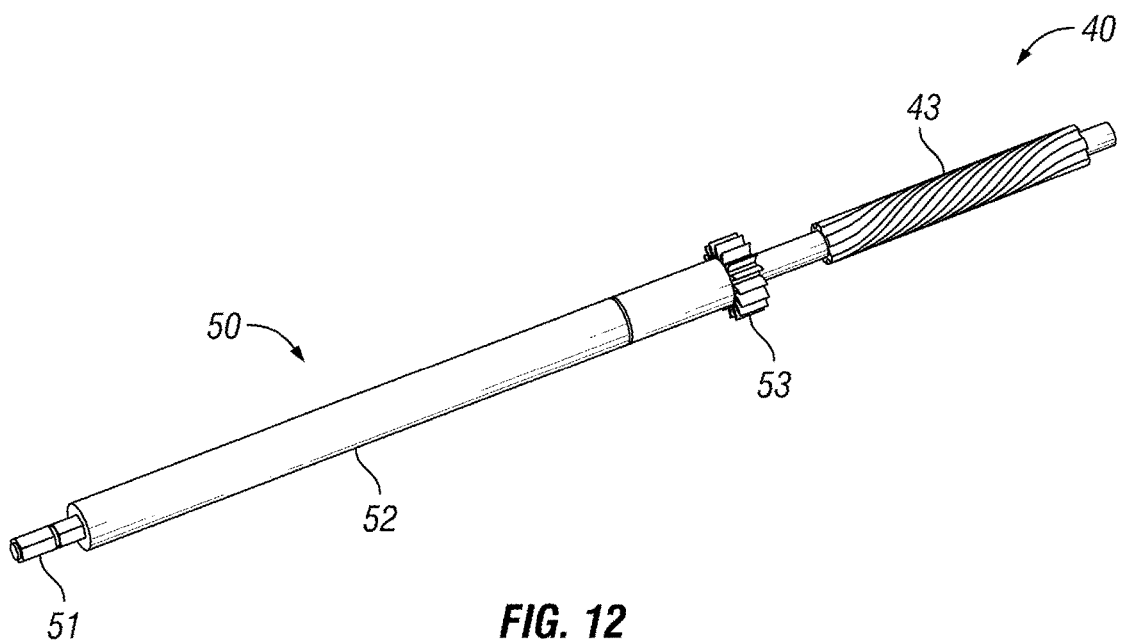

The boss reamer 50, as depicted in FIG. 12, may include a cannulated shaft 52 that includes a boss reamer head 53 at one end. The other end 51 of the shaft 52 may be configured to interface with a torque applying device, such as the chuck of a drill. The internal diameter of the cannulated shaft 52 is such that the shaft 52 may be slid over the IM reamer shaft, but generally not the IM reamer head, and rotated with respect to the IM reamer. The boss reamer head may also be cannulated to slide over the IM reamer shaft 42 and may have a cutting diameter substantially similar to the diameter of the central body 11.

The reamer guide assembly 60, as depicted in FIGS. 13-19, may include a trial stem 70 and a reamer guide 80. The reamer guide generally includes a base 82, a support shaft 81, and a guide block 88. The trial stem 70 may be connected to one end of the base 82. In one embodiment, this connection may be a threaded connection, ball-detent connection or any other connection as is known in the art. The other end of the base 82 includes an abutment surface 89 and the support shaft 81 extending from the base 82 at an outward angle with respect the longitudinal axis of the trial stem 70. The support shaft 81 then bends such that the remainder of the support shaft 81 is generally parallel to the longitudinal axis of the trial stem 70. Integrated into the end of the guide shaft 81 is the guide block 88. The guide block 88 generally includes a handle hole 83 extending through the guide block 88 for receipt of an alignment handle 90 (described below), an alignment pinhole (not shown) for receipt of an alignment pin 100 (described below), and a first and second lobe reamer guide 84, 85. The first and second lobe reamer guides 84, 85 are generally disposed between the handle hole 83 and alignment pinhole. Both the first and second lobe reamer guides 84, 85 include a passageway 86a, 86b that is substantially cylindrical and a side-slot 87a, 87b extending through the sides of each of the lobe reamer guides 84, 85 into the passageway 86a, 896b. The longitudinal axes of the passageways 86*a*, 86*b* extend to a location on the abutment surface 89. Further, these longitudinal axes may be provided at various angles with respect to the longitudinal axis of the trial stem 70 in order to ream different bone void dimensions.

The alignment handle 90, as depicted in FIG. 14-19, is generally an elongate shaft with a flange disposed 91 along its length for abutting against the guide block 88. The alignment pin 100 is preferably a ⅛" diameter pin with a length long enough to extend beyond the epicondyles when inserted into the guide block 88. While ⅛" diameter is preferred so as to not obstruct the epicondyles from the operator's view, any diameter pin may be used.

The lobe reamer assembly 110, as depicted in FIGS. 15-17 and 19, includes a lobe reamer head 117, a reamer shaft 116, a depth stop collar 112, and a bushing 113. The lobe reamer head 117 is disposed at one end of the reamer shaft 116, while the other end 111 of the shaft 116 is configured to interface with a torque applying device. The depth stop collar 112 is fixed to the reamer shaft 116 opposite the end of the lobe reamer head 117. The reamer shaft 116 has a diameter small enough to fit through the side-slot 87*a*, 87*b* of the first and second reamer guides 84, 85. The bushing 113 is disposed along a portion of the reamer shaft 116 between the reamer head 117 and depth stop collar 114 such that the bushing 113 can slide back and forth between the reamer head 117 and depth stop collar 112. The bushing 113 is generally cylindrical and includes a first segment 115 and second segment 114 where the second segment 114 generally has a larger diameter than the first segment 115. The diameter of the first segment 115 may be dimensioned to slide into and fit tightly within the passageway 86*a*, 86*b* of the first and second lobe reamer guides 84, 85.

Figure 18:
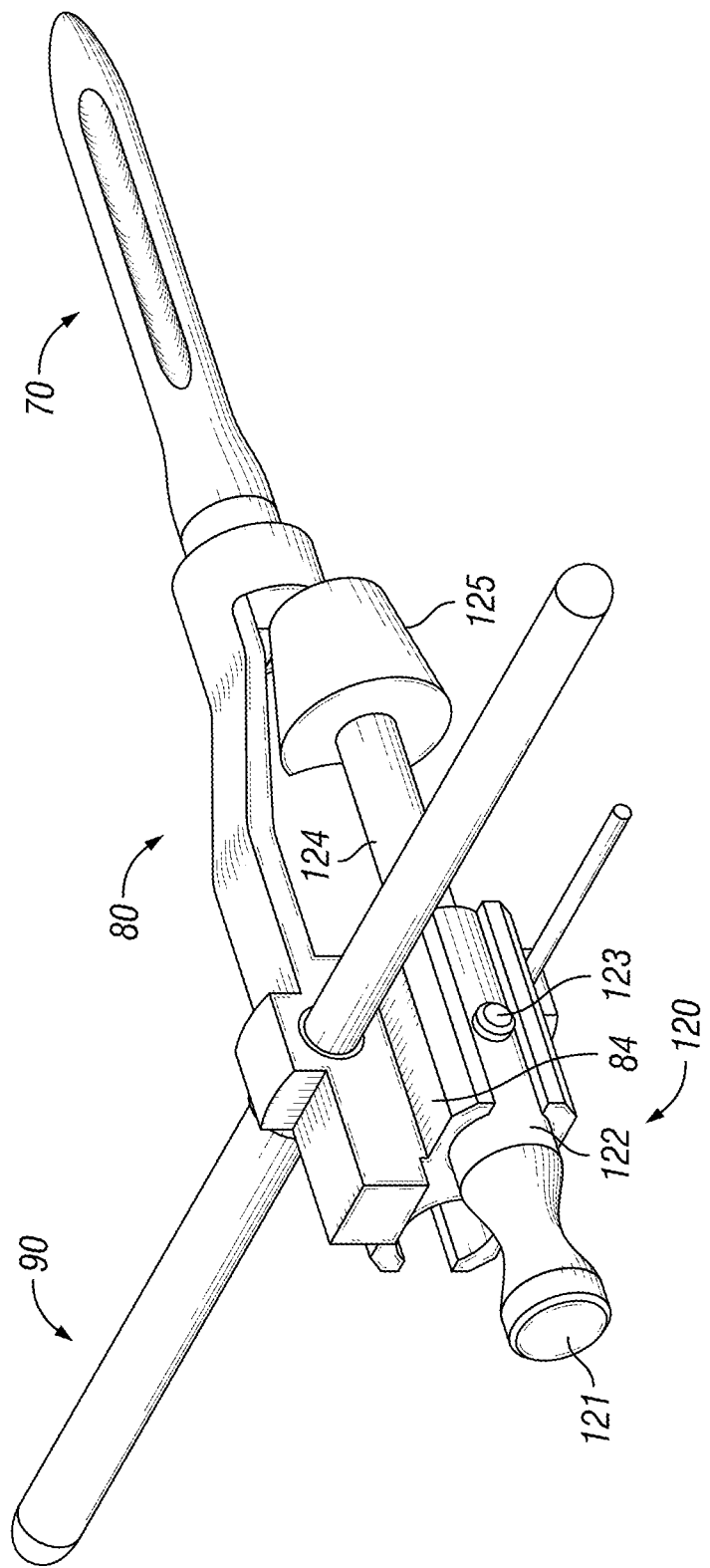
Figure 19:
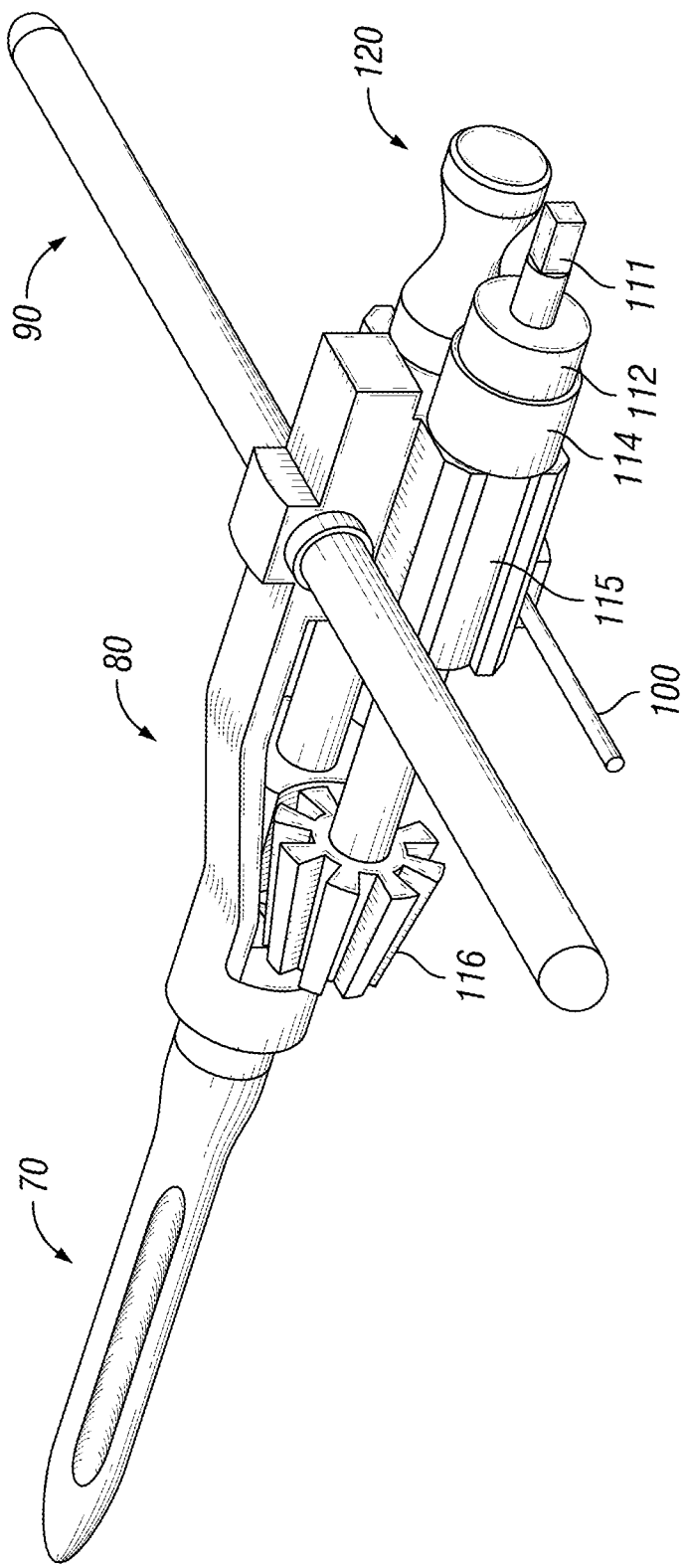

The lobe trial 120, as shown in FIGS. 18 and 19, includes a lobe trial head 125 and a first shaft segment 124 and a second shaft segment 122. The lobe trial head 125*d* is disposed at the end of the first shaft segment 124 and generally has a frustoconical shape with a portion removed along its length. The lobe trial head 125 is dimensioned to substantially match the bone void formed by the reamer head 116 and to substantially match at least one leg 12, 13 of the void filling prosthesis 10. While the lobe trial head 125 is depicted as having this shape, the lobe trial head 125 may have any shape depending on the shape of the reamer head 116 and the legs 12, 13 of the void filling prosthesis 10. The first shaft segment 124 has a diameter less than that of the second shaft segment 122 and is dimensioned to be capable of passing through the side-slot 87*a*, 87*b* of the first and second lobe reamer guides 84, 85. The second shaft segment 122 is dimensioned such that it can tightly fit and slide within the passageway 86*a*, 86*b* of the first and second lobe reamer guides 84, 85. An impact surface 121 is formed at the opposite end of the lobe trial 120 as that of the lobe reamer head 125. The impact surface 121 is a relatively broad and flattened surface so that the operator can impact the lobe trial 70 in order to seat the lobe trial head 125 into a bone void.

In one embodiment of the present invention, a method for forming a void in bone to receive the void filling prosthesis 10, as illustrated by FIGS. 11-19. In this embodiment, the instruments, as described above, are utilized. While FIGS. 11-19 and the following description of the method are directed toward the preparation of a bone void within a femur, it is to be understood that this is merely an example. The following method may be utilized to prepare a bone void in any long bone.

Referring to FIG. 11, the IM reamer 40 is depicted as reaming along the IM canal of a femur 200 until the bone 200 is flush with the requisite depth indicator 44. While it appears from FIG. 11 that the IM reamer 40 is passing through a femoral component, the femoral component is merely a depiction of the femur 200. With the IM reamer 40 remaining within the IM canal, the boss reamer 50 is slid over the shaft of the IM reamer, as shown in FIG. 12. The operator reams along the IM reamer shaft 42 until the boss reamer head 53 abuts the IM reamer head 40, thereby preventing further travel into the femur bone 200. The IM reamer and boss reamer 50 are then removed from the IM canal in preparation for further bone forming.

Figure 13:
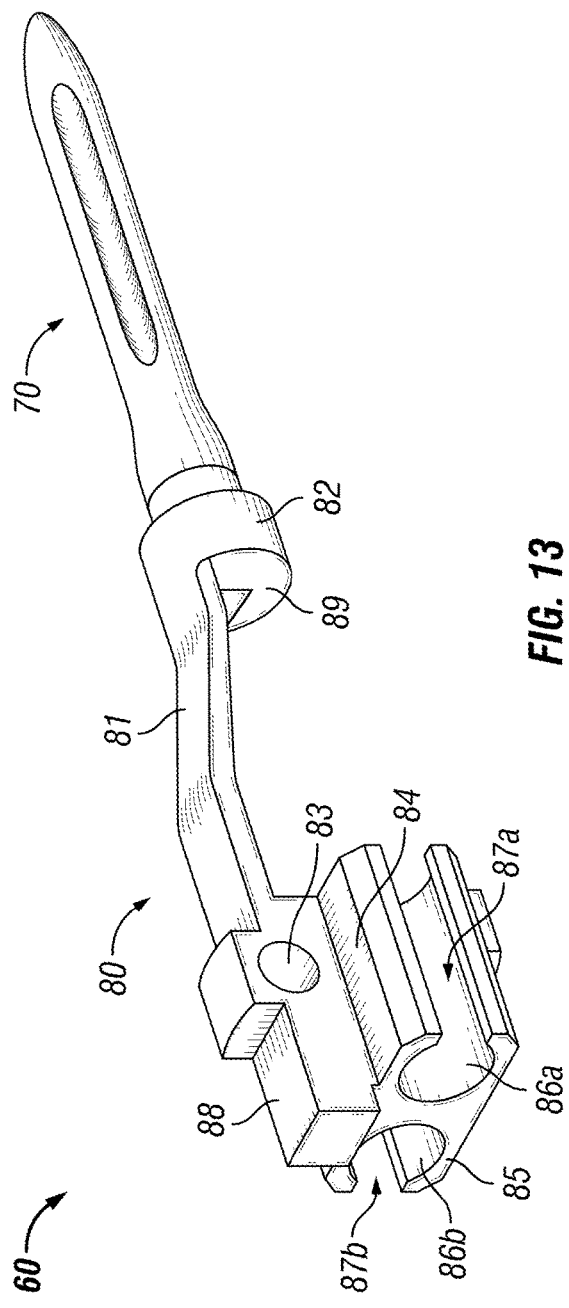

Referring to FIG. 13, the reamer guide assembly 60 is assembled. In such assembly, the operator may select a trial stem 70 to match the IM reamer head diameter, and then attach the trial stem 70 to the reamer guide 80. In another embodiment, the IM reamer 40 may be attached to the reamer guide 80, thus taking the place of the trial stem 70. Attachment may be by a threaded engagement, with a ball detent, or any other engagement known in the art. Once the reamer guide assembly 60 is assembled, the trial stem 70 is inserted into the portion of the IM canal that was reamed by the IM reamer 40, and the base of the reamer guide 82 is inserted into the portion of bone reamed by the boss reamer 50. The operator may further seat the reamer guide assembly 60 to the proper depth by impacting the end of the guide block 88. The proper depth may be indicated when the reamer guide assembly 110 no longer moves when impacted and generally where the bone is flush with the bend in the support shaft 81.

Figure 14:
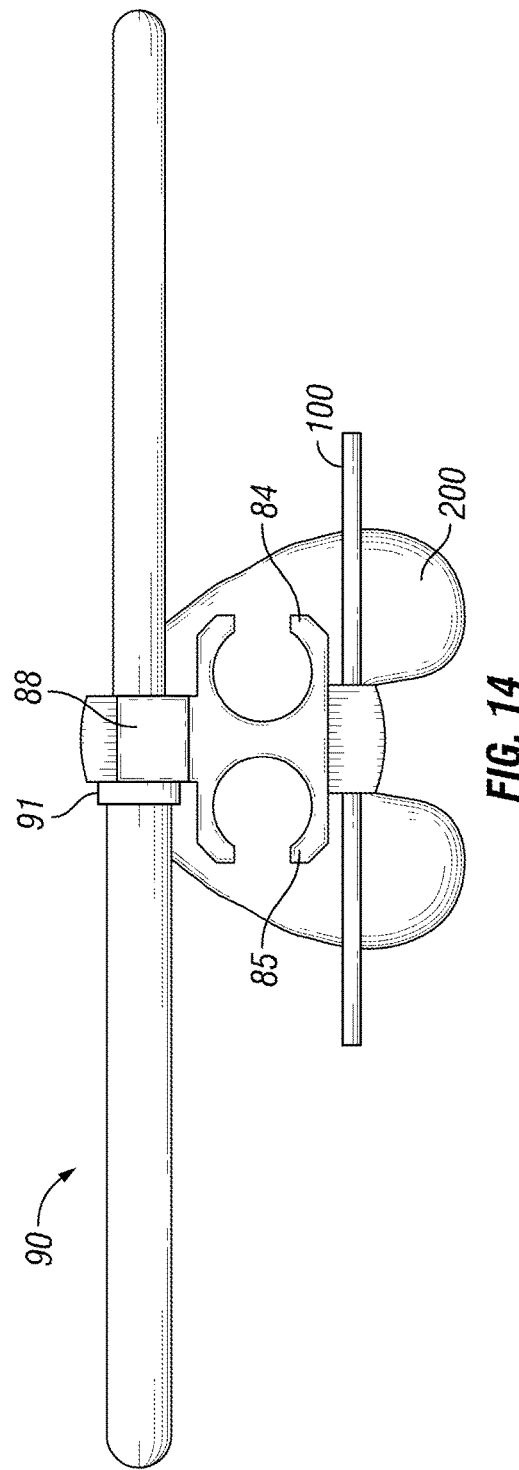

Referring to FIG. 14, with the reamer guide assembly 60 firmly seated within the IM canal, the alignment handle 90 is placed in the handle hole 83 until the flange 91 abuts the guide block 88, and the alignment pin 100 is placed in the alignment pinhole such that the alignment pin 100 extends from both sides of the guide block 88 beyond the periphery of the femur. The operator will then grip the alignment handle 90 and rotate the reamer guide assembly 60 within the IM canal until the alignment pin 100 is aligned with the transepicondylar axis or any axis of the operator's preference.

Figure 15:
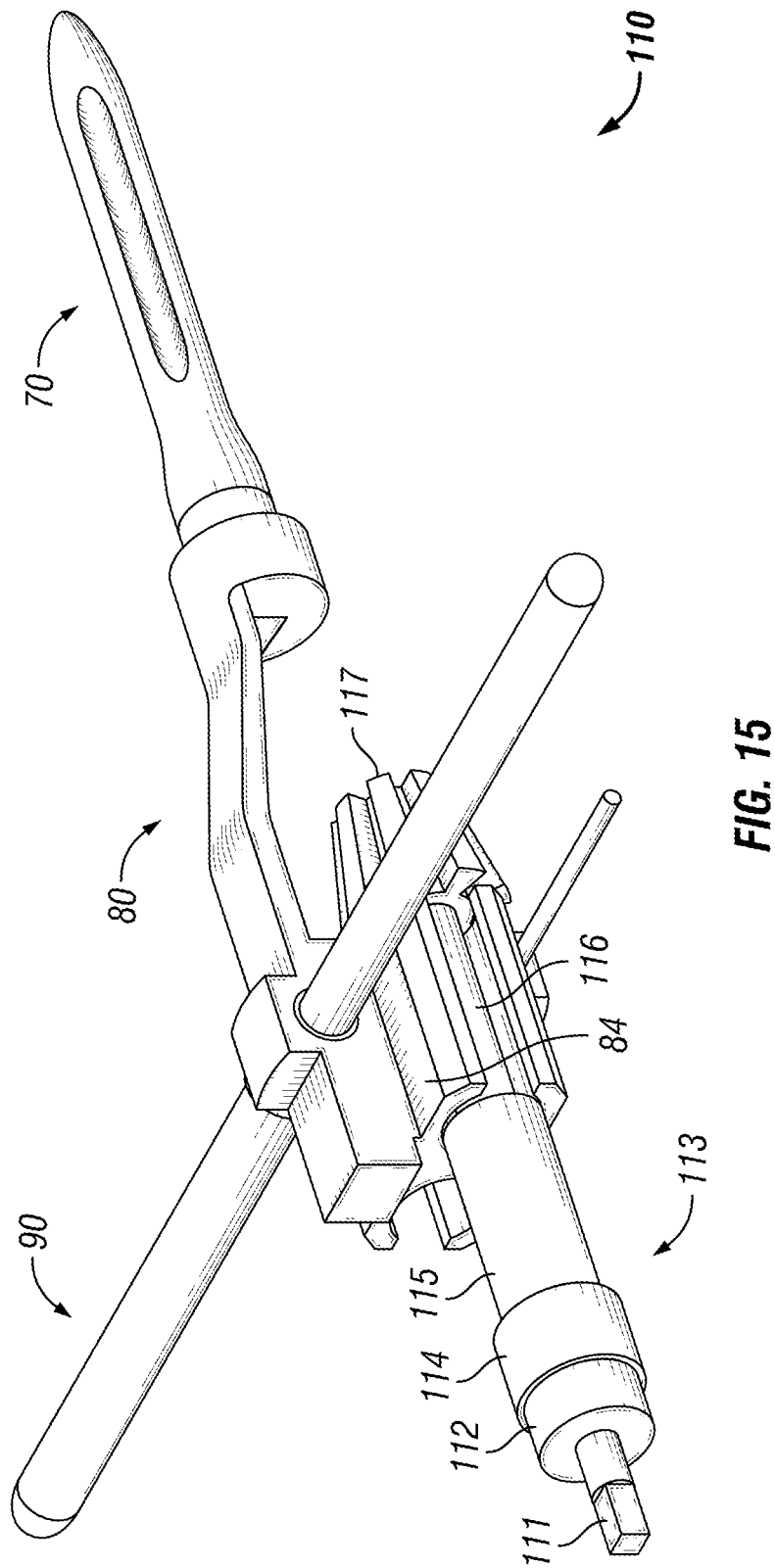
Figure 16:
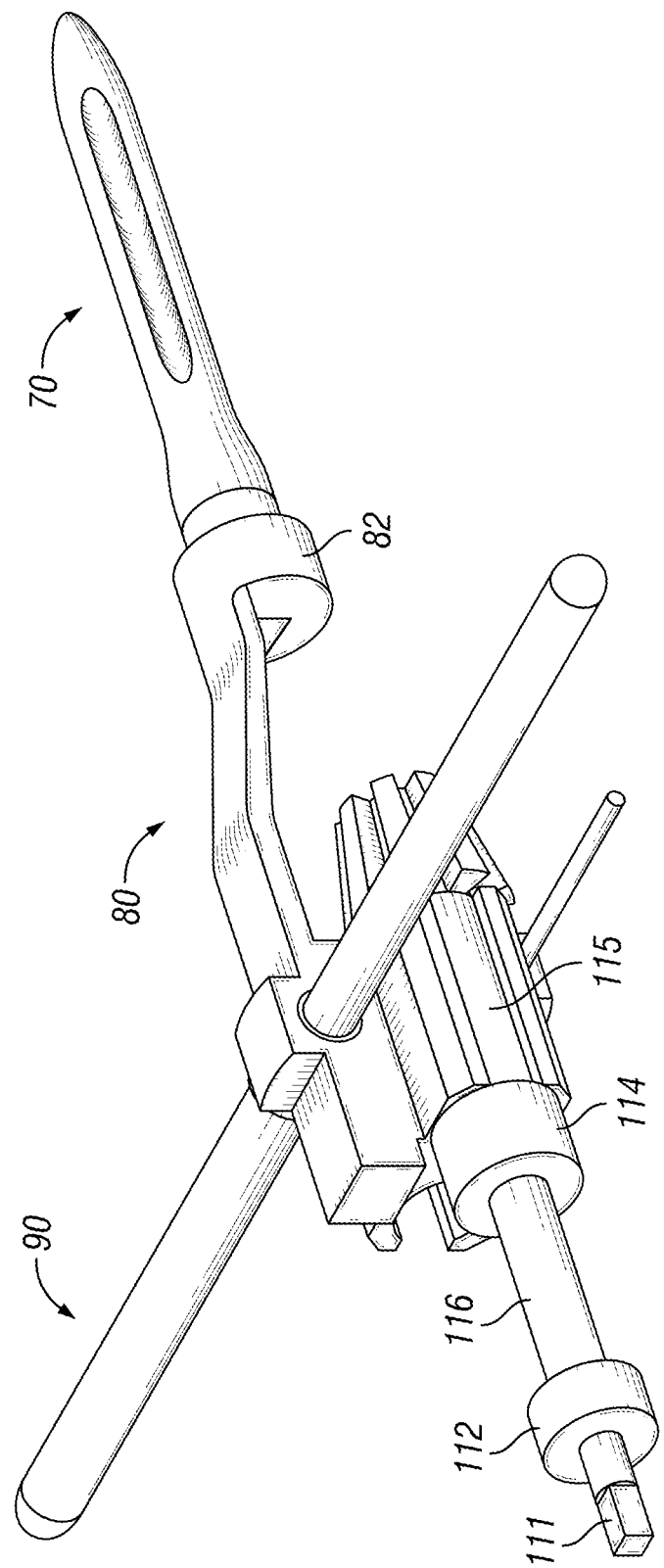
Figure 17:
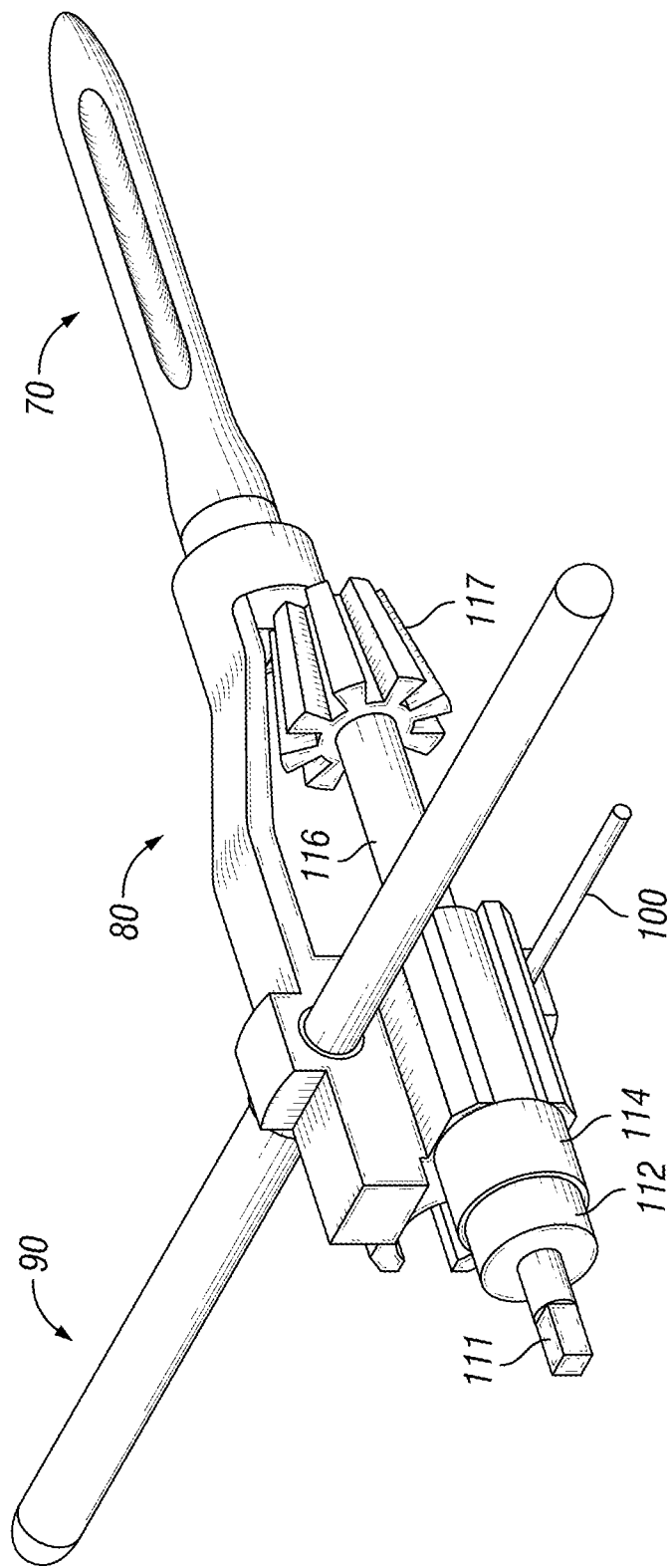

Referring to FIG. 15, once alignment is achieved the lobe reamer assembly 110 is loaded into the first lobe reamer guide 84. This is achieved by moving the bushing 113 so that it abuts the depth stop collar 112, thereby exposing the reamer shaft 116 proximate to the reamer head 117. The reamer shaft 116 is then side-loaded through the side-slot 87*a* and into the passageway 86*a*. The resulting configuration should be such that the reamer head 116 is located on one side of the first lobe reamer guide 84 and the bushing 113 located on the other side, as shown in FIG. 15. The first segment 115 of the bushing 113 is then slid into the passageway 86*a* until the second segment 113 abuts the first lobe reamer guide 84, as shown in FIG. 16. The reamer head 116 is then advanced into the distal femur by applying a torque to the reamer shaft 115 until the depth stop collar 112 abuts the bushing 113 and the reamer head 116 abuts the abutment surface 82, as shown in FIG. 17. The reamer head 116 is then retracted from the femur and the reamer assembly 110 removed from the first lobe reamer guide 84 through the side-slot 87*a*.

Referring to FIG. 18, the lobe trial 120 is then loaded into the passageway 86*a* of the first lobe reamer guide 84 in a similar fashion as the lobe reamer assembly 110. The first shaft segment 124 of the lobe trial 120 is passed through the side-slot 87*a* and into the passageway 86*a*. The lobe trial head 125 is then advanced into the first bone void. As the lobe trial head 125 is advanced, the second shaft segment 123 is advanced into the passageway 86*a* and the lateral protrusion 123 is advanced into the side-slot 87*a*. The lateral protrusion 123 ensures that the lobe trial 120 has the proper rotational alignment and also acts as a stop to prohibit rotation. In one embodiment of the lobe trial 120, the lateral protrusion 123 may be a pin that extends through the second shaft segment 122 and into a hole located in the first lobe reamer guide 84 to prevent both rotational and translational movement. The operator may then impact the impact surface 121 to fully seat the lobe trial 120. The lobe trial 120 may remain in place while a second bone void is formed in order to provide additional stability during reaming, as seen in FIG. 19.

Referring to FIG. 19, the lobe reamer assembly 110 is side-loaded into the second lobe reamer guide 85 as previously described. The reamer head 117 is then advanced into the distal femur by applying a torque to the reamer shaft 116 until the depth stop collar 112 abuts the bushing 113 and the reamer head 117 abuts the abutment surface 89, thereby forming a second bone void for receipt of the void filling prosthesis 10.

While this method has generally been described herein as utilizing one lobe reamer assembly 120 to form both bone voids, more than one lobe reamer assembly 110 having different geometries may be used depending on the geometry of the void filling prosthesis 10.

FIGS. 20-23 depict another embodiment void filling prosthesis 210, which is similar to the void filling prosthesis 10 previously described but differs in that an entire leg may be selectively removed.

As shown, void filling prosthesis 210 includes a central body 211, a lateral leg 212 and medial leg 213. Central body 211 is shown as being generally cylindrical and including an aperture 218 extending therethrough, like in the void filling prosthesis embodiments previously described herein. The central body 211 can be made from various materials including titanium, titanium alloy, stainless steel, cobalt chrome alloys, tantalum, or niobium. In addition, these materials may be provided in various forms, such as in a solid or porous form, for example, in the form of metallic foam.

In a preferred embodiment, the central body 211 includes an inner sleeve 217 (best shown in FIGS. 20 and 23) constructed from a solid material and an outer shell 216 (best shown in FIGS. 21 and 22) constructed from the same material in porous form to facilitate bony ingrowth. As an example, the inner sleeve 217 may be constructed from solid titanium and the outer shell 216 may be constructed from titanium foam. The inner sleeve 217 is generally the inner support structure for the central body, with the solid construction of the inner sleeve 217 providing structural support to a porous outer shell 216 and a bearing surface for an implant stem (not shown).

In other embodiments, the central body 211 can be constructed entirely of one material in one form. For example, the central body 211 may be constructed entirely of a solid titanium or titanium foam. In another embodiment, the central body 211 may be constructed from different materials and different forms. For example, the inner sleeve 217 can be constructed from solid tantalum and the outer shell 216 can be constructed from titanium foam.

Central body 211 also includes a first end, a second end and an intermediate member 214 coupled to the second end. In some embodiments, intermediate member 214 may be a separate structure mechanically coupled to the second end of the central body 211, for example via a welded connection or an adhesive. In other embodiments, the intermediate member 214 may be integrated into the central body 211 to form a monolithic structure, for example by building both structures together layer-by-layer or molding the structures together as a unitary structure. In either embodiment, the intermediate member 214 is preferably sized and shaped to conform substantially to the central body 211 such that there may be a smooth transition between the intermediate member 214 and central body 211.

The intermediate member 214 can be constructed from the same materials and forms as that previously discussed in relation to the central body 211. In a preferred embodiment, the intermediate member 214 is constructed from a porous material that has a porosity larger than that of the outer shell 216 of the central body 211. Generally, the intermediate body's construction is selected to facilitate connection of legs 212 and 213 to the central body 211 and to allow for ease of separation of legs 212 and 213 from the central body 211 when desired. As such, the porous material used in constructing the intermediate member 214 may include spaces or cells (not shown) that are both large relative to that of the central body's materials and predeterminately arranged in a uniform pattern, rather than randomly distributed throughout the material. This uniform pattern and large porosity relative to that of the central body 211 may facilitate penetration of a cutting device and provide for a smooth and uniformly cut surface. In one example, the cells of the porous material can be polygonal like that of a honeycomb or like a hollow rectangular prism. Thus, in one embodiment, the intermediate member can be constructed from titanium honeycomb or from titanium arrayed with adjacently situated, hollow rectangular prisms. These polygonal-like cells may provide structural strength while allowing the walls (not shown) making up each cell to be thin to facilitate ease of cutting.

In an alternative embodiment, the intermediate member 214 can be constructed from a metallic material with a lower modulus to that of the central body 211 and/or lateral and medial legs 212, 213 to facilitate ease of cutting and to help prevent cutting penetration of the central body 211 and/or the lateral and medial legs 212, 213. In another embodiment, the intermediate member 214 may have an identical construction to that of the central body 211 or be made entirely from metallic foam.

The lateral and medial legs 212, 213 have a similar profile to the lateral and medial legs 12, 13 previously described herein in order to conform to predictably shaped bone voids formed by generally cylindrical reamers and to communicate with a femoral component. Each leg 212, 213 is formed by a portion or portions of a support member 220 (discussed more fully below) covered with a bone interface member 230.

Figure 21:
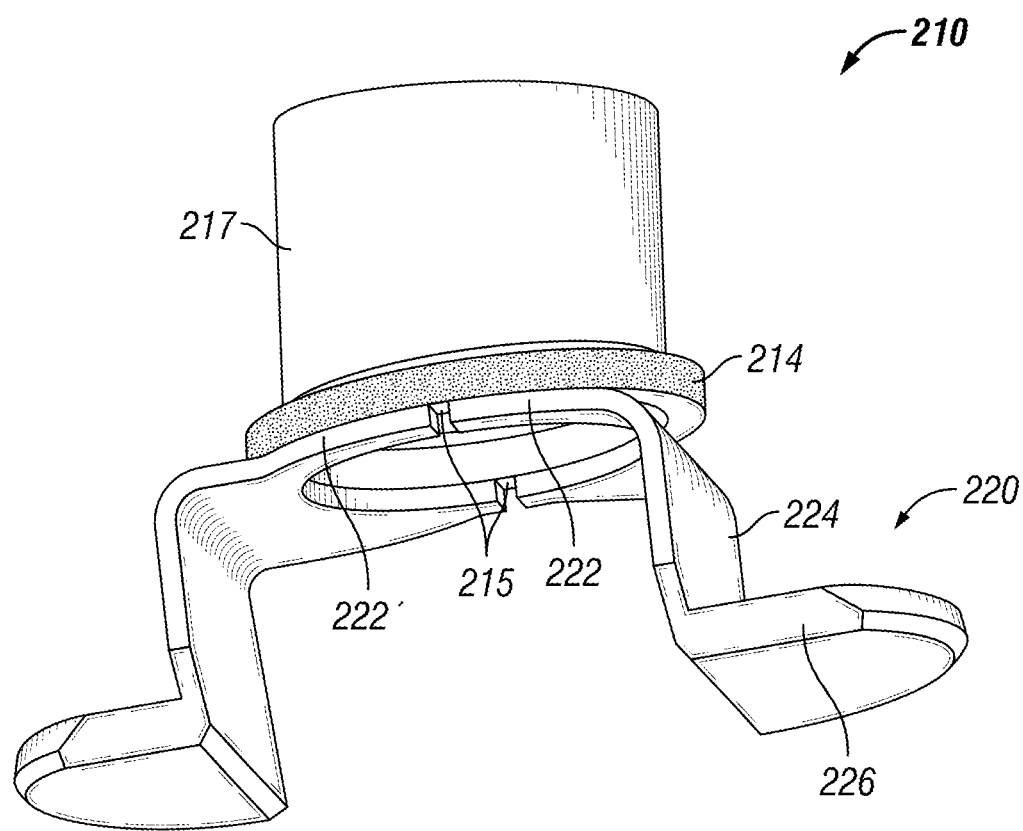
FIG. 21 shows a partially schematic perspective view of the void filling prosthesis of FIG. 20 having an intermediate member.
Figure 22:
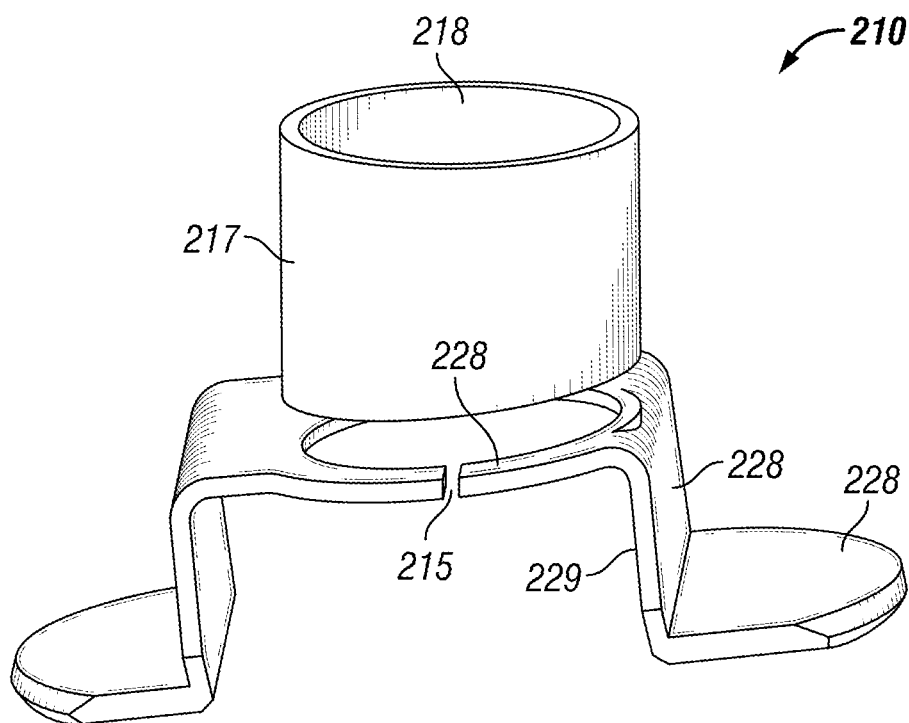
FIG. 22 shows a partially schematic perspective of the void filling prosthesis of FIG. 20 absent the intermediate member.

As best shown in FIGS. 21 and 22, the support member 220 includes an upper portion 222, a middle portion 224, a lower portion 226, an inner surface 228 and outer surface 229. In some embodiments, the support member 220 may only include the upper portion 222 and middle portion 224, or may only include the upper portion 222. As depicted, the upper portion 222 and lower portion 226 join the middle portion 224 to form a z-like configuration. The upper portion 222 is semi-cylindrical and has an inner radius similar to the inner radius of the intermediate member 214. The middle and lower portion 224, 226 are preferably dimensioned and shaped to conform to the periphery of the bone interface member 230.

The bone interface member 230 generally interfaces with the bone when implanted, while the support member 220 generally communicates with a femoral component when implanted and supports the bone interface member 230 in a connection with the central body 211 via the intermediate member 214. The support member 220 includes generally planar inner and outer surface 228, 229 to make way for the femoral component, and the bone interface member includes generally curved surfaces to conform to the bone.

In some embodiments, the bone interface member 230 may be a separate structure mechanically coupled to the inner surface 228 of the middle and lower portions 224, 226 of the support member 220. In other embodiments, the bone interface member 230 may be integrated into the support member 220 to form a monolithic structure, for example by building both structures together layer-by-layer or molding the structures together as a unitary structure.

The lateral and medial leg 212, 213 can be constructed from any of the materials and forms previously described in relation to the central body 211 and intermediate member 214. In a preferred embodiment, the support member 220 of each leg is constructed from a solid material and the bone interface member 230 is constructed from a porous material. As an example, the support member 220 may be made from solid titanium, and the bone interface member 230 may be made from titanium foam.

In an alternative embodiment, the support member 220 and bone interface member 230 may be made from one material in one form. For example, the support member 220 and bone interface member 230 may be made entirely from metallic foam. In another embodiment, the support member 220 and bone interface member 230 of each leg 212, 213 can be constructed from different materials and different forms. For example, the support member 220 may be made from solid tantalum while the bone interface member 230 may be constructed from titanium foam. In yet another embodiment, the lateral and medial leg 212, 213 may be constructed as that previously described in relation to void filling prosthesis 10, wherein the lateral and medial legs 212, 213 include selectively removable portions for reducing the length of a select leg.

The upper portion 222 extends outwardly from its respective leg 212, 213 in a cantilevered fashion and is coupled to the intermediate member 214 at the inner surface 228 of the upper portion 222. Such connection occurs substantially along a plane to facilitate separation between the intermediate member 214 and the upper portion 222, which may result in the removal of a leg. Separation may also be facilitated by a gap 215 formed between the upper portion 222 of the lateral leg 212 and the upper portion 222' of the medial leg 213, which allows separation of a single leg to occur by cutting along a single plane. In other words, the lateral leg 212 and medial leg 213 may be separate structures attached to the intermediate member 214, with a gap 215 formed therebetween. In certain embodiments, the legs 212, 213 may be formed as a unitary structure in that both legs 212, 213 may be directly connected to each other with no gap being formed. In such a case, where it would be desirable to remove only the lateral leg 212 or only the medial leg 213, separation may be achieved by cutting between the intermediate member 214 and upper portion 222 as well as at a location somewhere between the lateral and medial leg 212, 213 in order to remove the leg. On the other hand, where the legs 212, 213 are separate structures forming a gap 215, separation may be achieved by cutting only between the intermediate member 214 and upper portion 222.

Additionally, gap 215 may extend into the intermediate member 214 or bisect the intermediate member 214. The extension of the gap 215 into the intermediate member 214 or bisection of the intermediate member 214 by the gap 215 may allow the operator to cut the intermediate member 214 along any plane extending through the intermediate member 214 to the gap 215, rather than only along a plane formed by the junction of the intermediate member 214 and each leg 212, 213.

Figure 20:
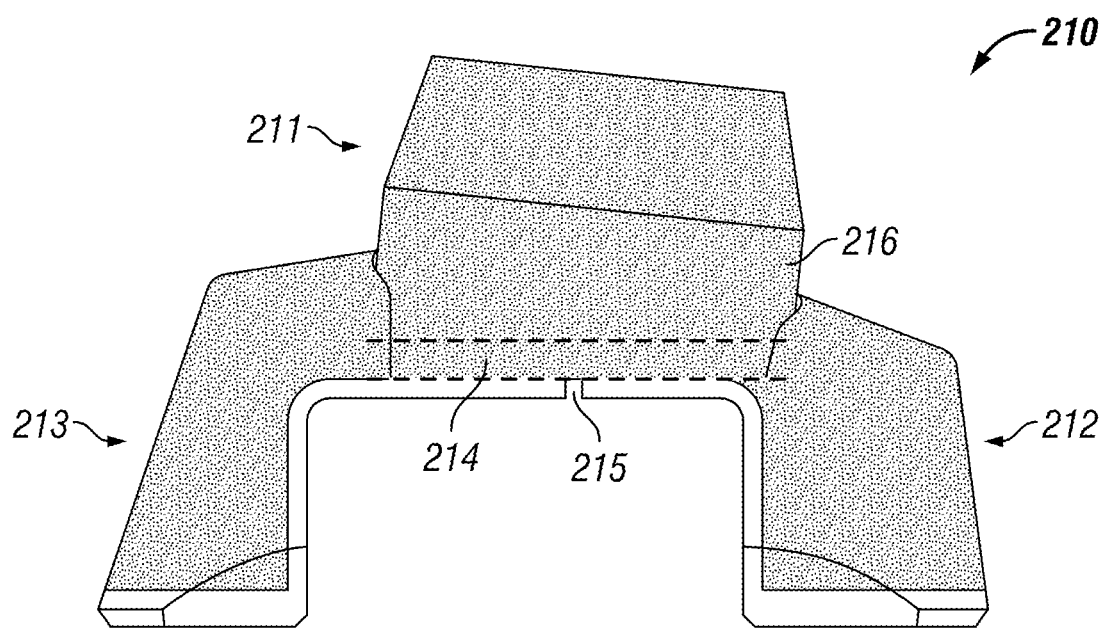
FIG. 20 shows a front view of another embodiment of the void filling prosthesis having selectively removable legs.
Figure 23:
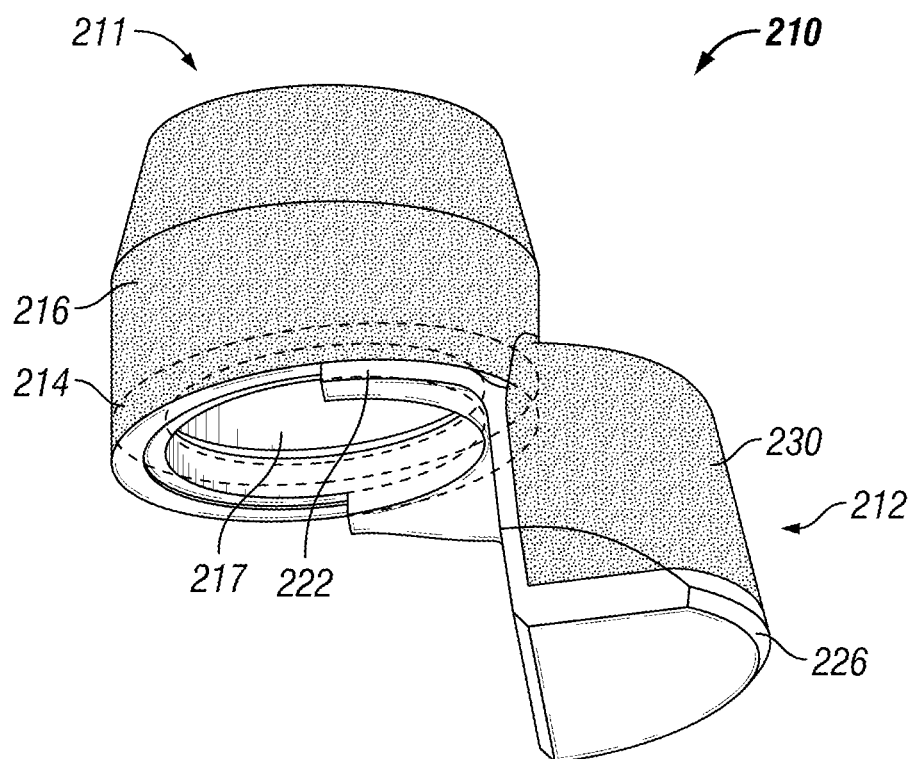
FIG. 23 shows a perspective view of void filling prosthesis of FIG. 20 absent a selectively removable leg.

Generally a lateral or medial leg 212, 213 may be removed through the use of a cutting device, such as that previously discussed herein and disclosed in U.S. application Ser. No. 12/002,002, the disclosure of which is hereby incorporated by reference herein, by cutting in an anterior-posterior direction. In some embodiments the bone interface member 230 may wrap around a portion of the intermediate member 214 partially obstructing the intermediate member 214 anteriorly and/or posteriorly as depicted in FIGS. 20 and 23. In such embodiments, the upper portion 222 of the support member 220 may attach to the intermediate member 214 at locations that are not obstructed by the bone interface member as illustrated in FIGS. 21 and 23, allowing an anterior-posterior cut to be performed along the junction between the intermediate member 214 and the upper portion 222 without going through or around the bone interface member 230.

While the aforementioned description and related figures describe a void filling device having selectively removable legs, it is contemplated that the selectively removable features of the first embodiment 10 may be combined with selectively removable lateral and medial legs of the present embodiment 210 providing an operator with the flexibility to reduce the length of a leg or entirely remove a leg.

Another aspect of the present disclosure includes methods of filling bone voids. During a knee revision procedure, an operator may remove the previously implanted prostheses. Generally, a central bone void extends into femur and/or tibia, and oftentimes unpredictably shaped bone deformities are formed adjacent to the central bone void by the incidental removal of bone during the implant removal process. Such bone deformities may interfere with the revision prostheses and may be rectified in a number of different ways including reaming the bone deformities to form predictably shaped offset bone voids as previously described herein and/or by removing a section of bone housing the deformity from the proximal tibia or distal femur.

Once the bone is shaped to account for bone deformities, the operator may assess the bone to determine the number of offset bone voids for filling with a void filling prosthesis. In some instances where there are less offset bone voids than there are legs associated with a void filling prosthesis 210, for example where only a lateral or only a medial offset bone void exists, the operator can remove a lateral or medial leg 212, 213 in order to correspond with the number of voids.

Generally, a cutting device, such as that previously discussed herein and disclosed in U.S. application Ser. No. 12/002,002, may be utilized to separate either the lateral or medial leg 212, 213 from the remainder of the void filling prosthesis. A planar blade may be inserted through the junction between the intermediate member 214 and the upper portion 222 and between the gap 215 and bone interface portion 30. Alternatively, the planar blade may be inserted through the intermediate portion 214 between the gap 215 and bone interface portion 230. The leg may be removed by cutting from an anterior and/or posterior direction. As previously mentioned, the intermediate member 214 is generally constructed of a softer material or a material with a larger porosity than the support member to facilitate visualization of the junction between the two members and to facilitate a smooth and easy cut resulting in a predictable surface.

Once the void filling prosthesis 210 has the desired number of legs, the operator may implant the prosthesis by inserting the central body 211 into a central bone void and the remaining leg(s) into the offset bone void(s).

Alternatively, where the offset bone voids equal the number of legs of the prosthesis as provided, the implant may be implanted without any removal of legs. On the other hand, where there are no offset bone voids, all of the legs may be removed and the central body 211 and intermediate member 214 may be inserted into the central bone void.

FIGS. 24A-27 depict alternative void filling prosthesis 300. Void filling prosthesis 300 is similar in certain respects to void filling prostheses 10 and 210. For example, prosthesis 300 similarly includes a central body 302, a first leg 304 and a second leg 306. Alternatively, prosthesis 300 may include a central body 302 and only the first leg or second leg 304, 306. Further, void filling prosthesis 300 can similarly fill a void formed by the methods previously described herein with relation to FIGS. 11-19. However, prosthesis 300 differs from prostheses 10 and 210 with respect to certain features and configurations of the central body and first and second legs.

Unlike central bodies 11 and 211, which are depicted as being ring-like or annular shaped such that each have an enclosed or encompassing circumference, central body 302 is open. This open central body 302 is defined by an aperture 308 that extends through the length of the body 302 and also through a sidewall along the body's entire length, which forms a "C" or "U" shaped cross-sectional profile. As such, central body 302 includes a curved portion 313 and a first wall portion 315 and second wall portion 317, which each adjoin the curved portion 313 at opposite locations. The curved portion 313 may be semicylindrical such that it has a constant outer and/or inner radius along the length of the central body 302. Alternatively, and preferably, the curved portion 313 has a frustoconical taper such that its outer and/or inner radius differs along its length. In some embodiments, the inner radius may be constant along the length of the body 302, while the outer radius may have a frustoconical taper, and thus a varying wall thickness, along the length of the body 302. In other embodiments, the central body 302 can have both a cylindrical portion and a frustoconical portion in a stacked arrangement.

The first and second wall portions 315, 317 may have planar inner and outer surfaces such that the cross-sectional profile of the inner and outer surfaces of the central body is U-shaped. In other embodiments, the first and second wall portions 315, 317 may each have a curved outer surface and a planar inner surface which may tangentially intersect an imaginary cylinder or conical frustum defined by the inner surface of the curved portion 313. Thus, in such embodiment, the wall thickness between the inner surface and outer surface of the central body 302 at the first and second wall portions 315, 317 may vary in order to allow for such planar inner surfaces and curved outer surfaces. The cross-sectional profile of the outer surface body 302 in such embodiment would be C-shaped, and the cross-sectional profile of the inner surface of the body 302 would be U-shaped. In another embodiment, the inner and outer surfaces of the body 302 at the first and second wall portions 315, 317 may be similarly curved such that the cross-sectional profile of the inner and outer surfaces of the body 302 may be C-shaped. The inner surface of the central body 302 may have three dimensional features, such as a stepped surfaces, to promote the securement of bone cement or other adhesives thereto. Where such features are included, the inner radius of the curved portion 313 is determined by the innermost regions of such features.

The radius of the curved portion 313 and the shortest distance between the first and second wall portions 315, 317 may be larger than the cross-sectional thickness of a stem 360 of a joint prosthesis such as to allow the placement of about at least a 2 mm cement mantle between the stem 360 and the inner surface of the central body 302. The aperture 308 of the central body 302 preferably extends through the sidewall in an anterior direction. However, the aperture 308 may extend through the sidewall in a posterior direction. The combination of the anterior or posterior opening in the sidewall along with dimensioning that allows for the placement of a cement mantle provides for the accommodation of many different size and shape stem components. Additionally, the space provided by the relatively larger dimensioning and the anterior or posterior opening in the sidewall provides operating-room flexibility in that it allows the operator to shift the stem 360 and joint prosthesis attached thereto in any number of directions so that the operator can more precisely position the articular surface of the joint prosthesis. In particular, the flexibility to shift the stem 360 in an anterior-posterior direction is beneficial in positioning the articular surface in order to achieve the desired flexion and extension gaps and to achieve the desired patellar tendon tension. Such flexibility also allows the operator to utilize offset stems without having to refit a new void filling prosthesis.

Figure 24A:
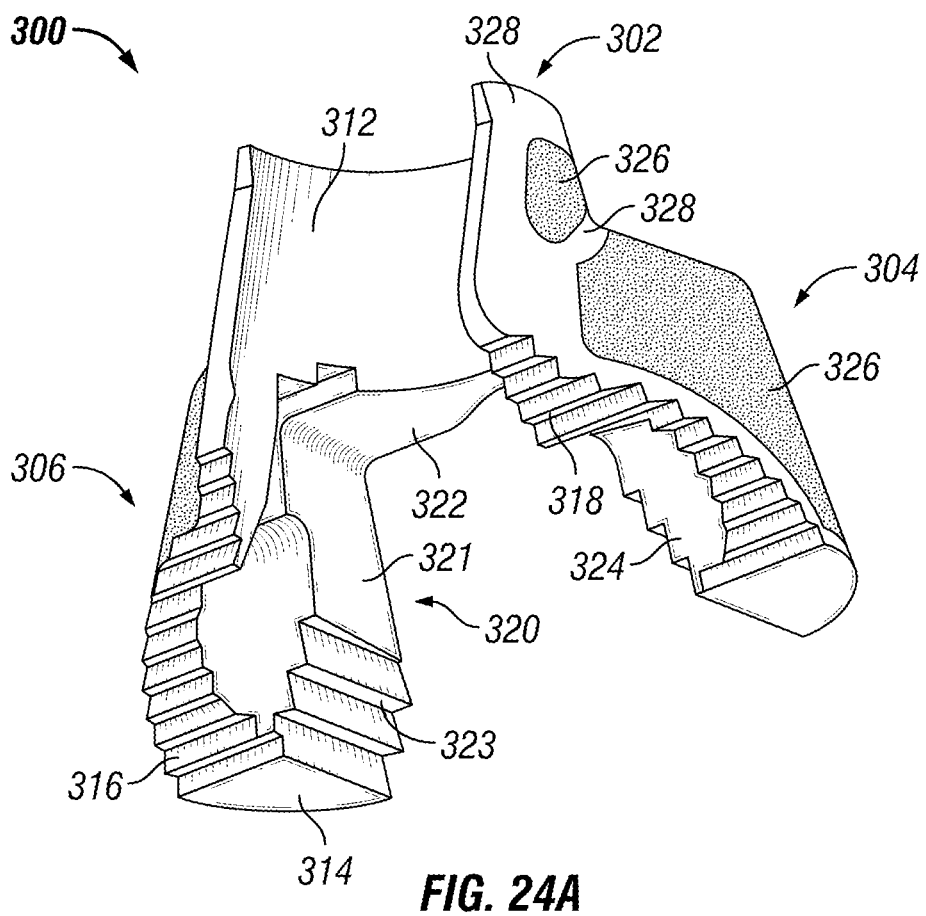
FIG. 24A is a front perspective view of an alternative void filling prosthesis.
Figure 25:
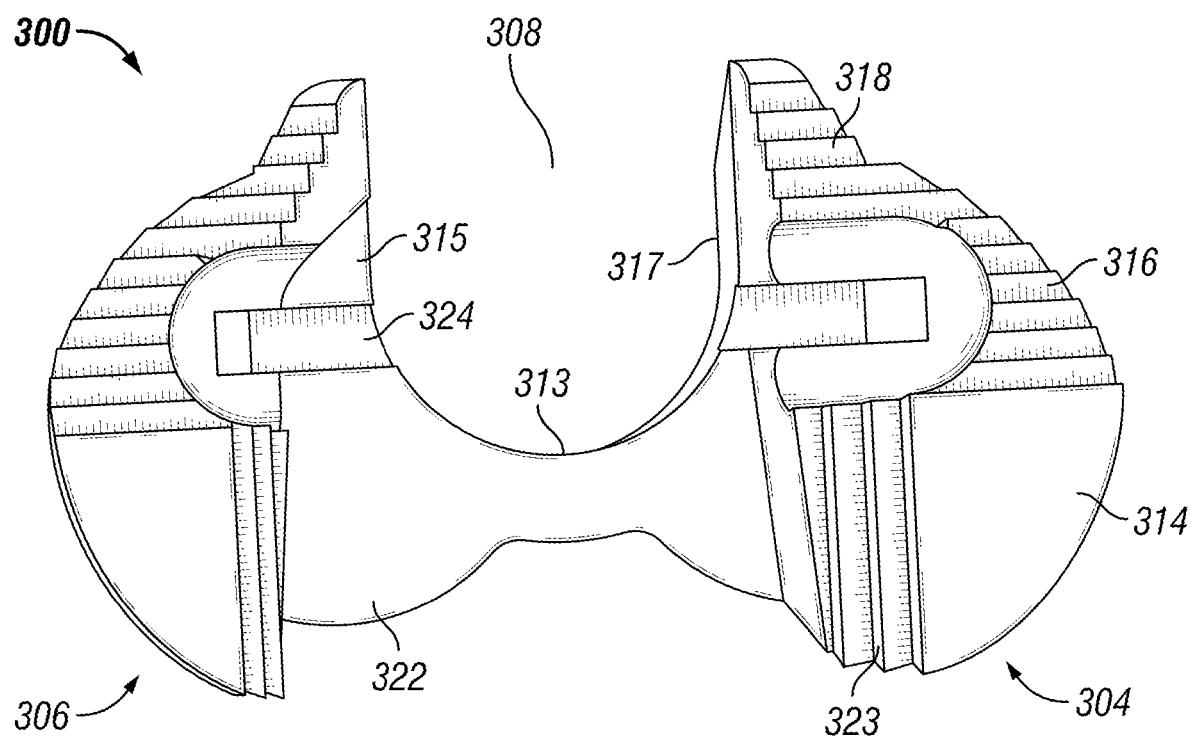
FIG. 25 is a bottom view of the void filling prosthesis of FIG. 24A.

Similar to the legs of prosthesis 10 and 210, the first and second legs 304, 306 may be offset posteriorly from a median transverse axis of the central body 302. Further, the first and second legs 304, 306 may be located in close proximity, but may be separated generally by a space 310 that penetrates through both legs and forms a saddle-like structure in order to provide clearance for a femoral cam box of a femoral component. This space 310 forms inner surfaces 320 and 322 that may abut the femoral cam box when implanted. As best shown by FIGS. 24A and 25, these inner surfaces include flat, planar sections 321, and stepped sections 323 to facilitate bonding with bone cement or other adhesive. Alternatively, these inner surfaces 320, 322 may only be planar and may include a textured surface for cement adhesion, or they may be entirely stepped. Further, inner surface 322 may be obliquely angled with respect to the longitudinal axis of the central body 302 in order to account for the angle of the IM stem 360 with respect to the surfaces of the cam box (not shown).

Further geometric features may be incorporated into the first and second legs 304, 306 in order to provide clearance for the structure of the femoral component and to also conform to the resected surfaces of the distal end of a femur bone so as to provide structural support to the bone as close to its outer boundaries as possible. For instance, each leg includes surfaces 314, 316, and 318, where each surface is angled with respect to each other such that, when implanted, such surfaces would be substantially coplanar to a distal, anterior chamfer, and anterior resected surfaces, 352, 354, 356, respectively (best shown in FIG. 27). These surfaces 314, 316, 318 are angled to coplanarly conform to these resected surfaces 352, 354, 356 that are formed in a typical five-cut femur (distal, anterior, posterior, and anterior/posterior chamfer resections). However, each leg 304, 306 could also have surfaces formed to coplanarly conform to a three-cut femur (distal, anterior, and posterior resections). For instance, surfaces 318 and 316 may be combined into one surface angled with respect to surface 314 in order to match the angle of an anterior resection with respect to a distal resection of a three-cut femur.

As shown, surfaces 316 and 318 are stepped to facilitate cemented fixation with a femoral joint prosthesis. Surface 314 is planar, but may be stepped and/or include a textured surface to facilitate cement adhesion. In some embodiments, each of these surfaces 314, 316, 318 may be planar, or any combination of stepped and planar.

Each leg 304, 306 also includes an impaction feature 324 that is a recess extending longitudinally into each leg 304, 306 from the distal end of each leg. These features are shaped to receive a complementary shaped impaction tool (not shown) that can tightly fit with the impaction feature 324 and allow the operator to uniformly impact prosthesis 300 into a void formed in the end of a bone.

The remainder of the first and second legs 304, 306 that has not been shaped to receive an impaction tool, conform to a femoral cam box, or conform to resected bone surfaces generally has a frustoconical profile. This geometric profile is preferred in order to conform closely to bone voids created by complimentary frustoconical reaming instrumentation. This frustoconical shape is additionally beneficial in that it allows for easy bone preparation utilizing a frustoconical reamer, and also provides a tapered bone contact surface, which facilitates a very tight press-fit fixation within the target bone. Additionally, the frustoconical profile of each leg can be the same as the frustoconical profile of the central body so that a single reaming device may be utilized to form the bone void to receive prosthesis 300.

However, frustoconical is merely an example of the type of geometry that the first and second legs 304, 306 may form. The legs 304, 306 may have other geometries, such as box-like geometries. Additionally, the first and second legs 304, 306 may be symmetric with respect to one another for universal fit into both a right and left limb, or they may be asymmetric where one leg 304, 306 may be larger than the other and/or one leg may have a different geometry for a limb specific configuration.

Void filling prosthesis 300 may be constructed from various metallic or polymeric biocompatible materials. For example, prosthesis 300 can be made from titanium, stainless steel, cobalt-chromium, tantalum, niobium, or polyethylene. Additionally, prosthesis 300 can have porous outer surfaces 326 for directly contacting bone to facilitate bony ingrowth into its porous structure. Preferably a portion of prosthesis 300 is formed from porous material and a portion is formed from solid material. Solid, as used herein, means that the porosity of its structure is unlikely to allow bone ingrowth therein.

Figure 24B:
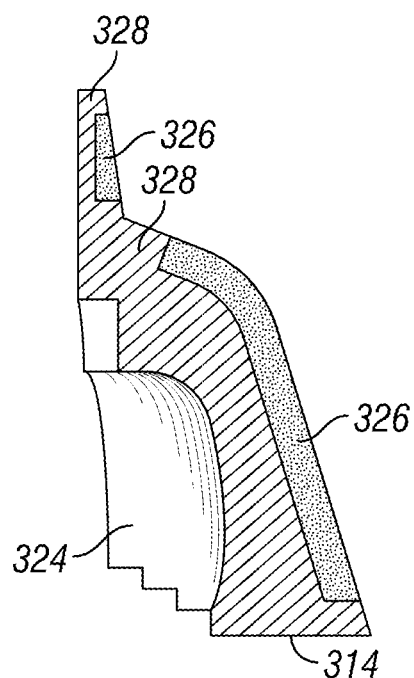
FIG. 24B is a highly schematic cross-sectional view of a leg and a portion of a central body of the void filling prosthesis of FIG. 24A illustrating a solid rim and porous outer surface.
Figure 26:
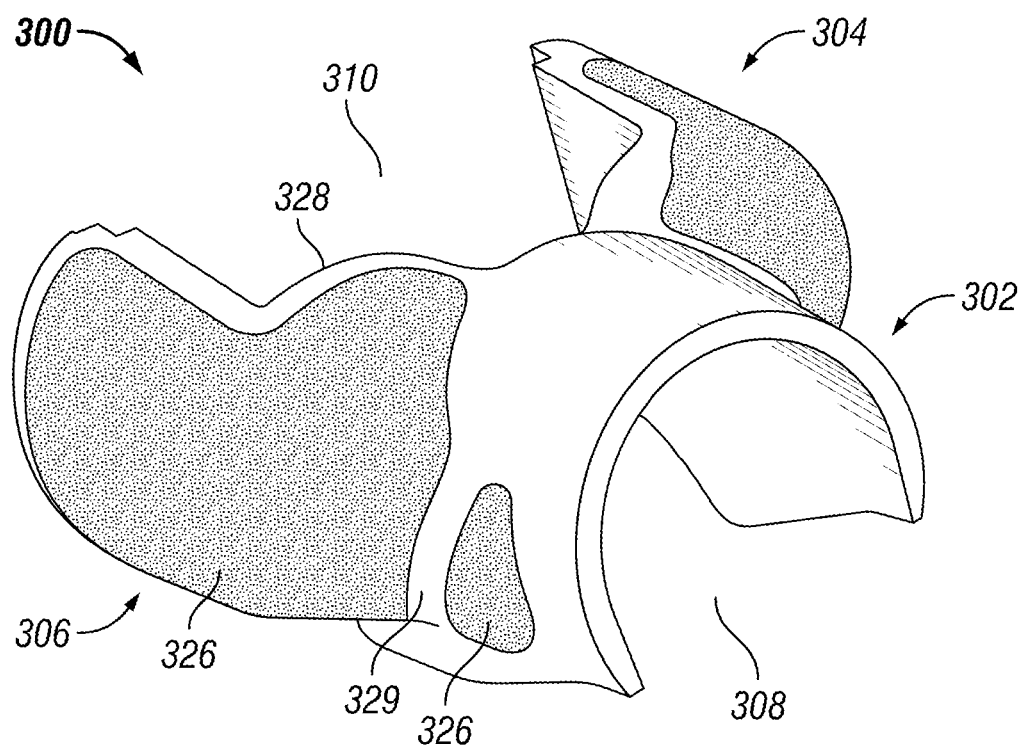
FIG. 26 is a top perspective view of the void filling prosthesis of FIG. 24A.
Figure 27:
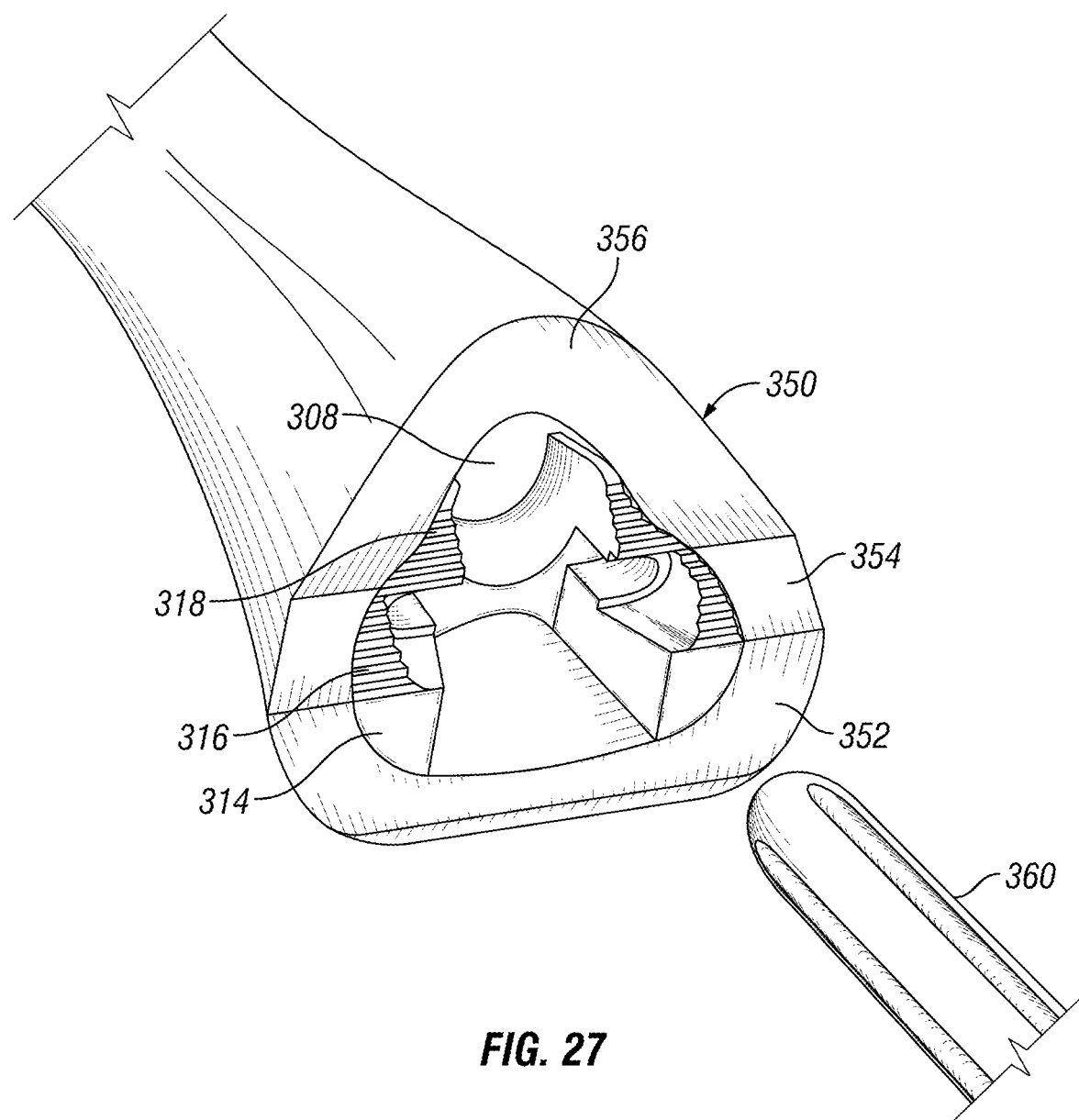
FIG. 27 is a depiction of the void filling prosthesis of FIG. 24A implanted into a femur bone.

As best seen in FIGS. 24A, 24B and 26, inner surface 312 of the central body 302 and surfaces 314-323 of the first and second legs 304, 306 are preferably solid, while the outer surfaces 326 that contact bone when implanted are preferably porous. Further, prosthesis 300 preferably includes a solid rim 328 that runs along the outer boundaries of the prosthesis and connects the outer surfaces 326 with the inner surfaces 312 and 314-323 of the prosthesis 300. The rim is preferably constructed from a solid material that spans the entire thickness of the prosthesis at the outer boundaries. Such boundaries may occur at intersections between bone contact surfaces and implant interfacing surfaces, that is, surfaces that directly contact or face the joint prosthesis or are connected to the joint prosthesis via adhesive. Other boundaries in which the solid rim may be found occur at the interface 329 between the central body 302 and legs 304, 306. The rim at this interface 329 may also be formed of solid material, which extends through the entire prosthesis thickness to reduce the risk of fracture at that junction. The solid rim 328 provides strength and structural support to the porous structure, particularly during impaction, and also helps to significantly reduce or eliminate potential sharp edges that can form where a hard porous structure comprises an outer boundary of an object. In some embodiments, the entire prosthesis 300 may be porous, or the legs 304, 306 may be entirely porous and the central body 302 entirely solid.

In some embodiments, the outer surface 326 of prosthesis 300 may also have discrete sections that are porous and discrete sections that are solid. This may be particularly useful where a patient's bone structure has significantly deteriorated to the point that the bone defects are no longer contained within the cortical bone. In this scenario, prosthesis 300 can take the place of the deteriorated cortical bone by providing discrete sections of the outer surface, or even entire legs, with solid material to act as cortical bone.

The porous and solid portions of prosthesis 300 may be precisely formed by SLM as described in the heretofore referenced applications incorporated by reference herein, for example, and could even be formed as patient specific in instances where the bone defects are known prior to the surgical procedure. Additionally, prosthesis 300 may be formed and provided in various sizes in conformance with a database that catalogues the specific anatomy of a selected population of individuals. As previously mentioned, the methods of forming a bone void previously described herein may be utilized in implanting prosthesis 300. As such, a frustoconical reamer may form a central void for receipt of the central body 302 and may form two adjacent and offset frustoconical voids for receipt of the first and second legs 304, 306. In some scenarios, where a bone defect only exists lateral or medial of the IM axis, a central void and only one offset void may be formed, and a prosthesis with a central body 302 and only one leg 304, 306 may be implanted therein. Implantation is achieved by connecting an impaction tool to the impaction feature 324 and using a mallet, or some other blunt instrument, to impact prosthesis 300 into the formed bone void. Generally impaction is ceased when surfaces 314, 316, 308 are coplanar with resected surfaces 352, 354, 356 of the bone 354. The tapered nature of the frustoconical voids and frustoconical central body 302 and legs 304, 306 provides a tight press fit such that all or most bone contact surfaces 326 are firmly pressed against the bone 350, which facilitates bony ingrowth into the porous structure.

Once prosthesis 300 is implanted, a joint prosthesis with a stem component 360 may be implanted. The stem 360 is inserted through the central body 302 where the operator has the freedom to adjust the stem 360 in multiple directions, particularly in an anterior-posterior direction to precisely seat the joint prosthesis onto the bone 350. Bone cement, such as polymethyl methacrylate, may be placed between the central body inner surface 312 and stem 360 and also along surfaces 314-323 to join the joint prosthesis with prosthesis 300 and bone 350. Stepped surfaces provided on surfaces 316, 318, and 323 and optionally 314, 321, and 322 help prevent the separation of cement at the prosthesis-cement interface under loaded conditions. As such, the stepped surfaces are generally formed such that the stepped surfaces taper outwardly in the direction of the loads under normal operating conditions.

Figure 28A:
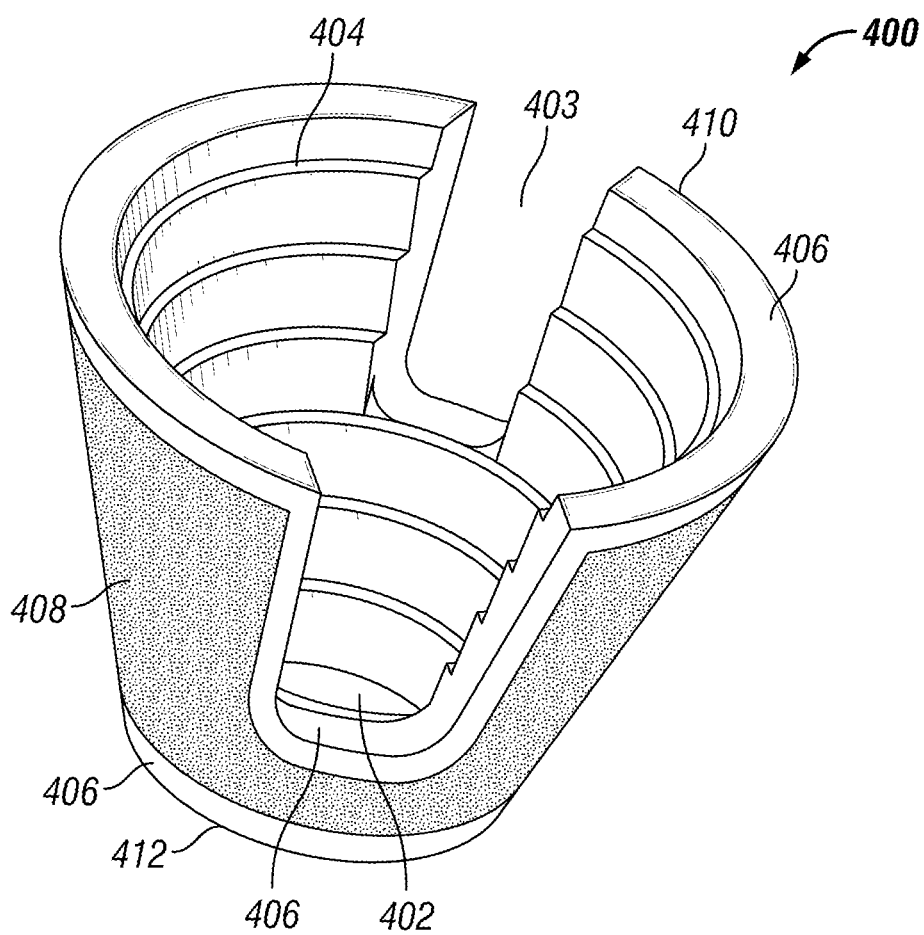
FIG. 28A is a front perspective view of yet another void filling prosthesis.

FIG. 28A depicts another void filling prosthesis 400. Void filling prosthesis 400 is frustoconical shaped and has an aperture 403 extending through its entire length. Recesses 402 extend through the sidewall of prosthesis 400 to provide free space in order to receive a keel of a joint prosthesis, such as a tibial baseplate prosthesis. The outer surface 408 of the prosthesis is preferably constructed of a porous material while the inner surface 404 is preferably solid. Additionally, the inner surface 404 may include a stepped surface to facilitate cement adhesion. The inner surface 404 generally tapers inwardly from the proximal end 410 to the distal end 412 and the stepped surfaces provide resistance to loads at the cement-prosthesis interface.

Figure 28B:
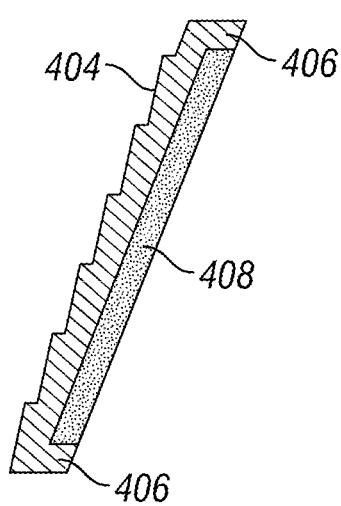
FIG. 28B is a highly schematic cross-sectional view of a portion of the void filling prosthesis of FIG. 28A illustrating a solid rim and porous outer surface.

Similar to prosthesis 300, a solid rim 406 is provided around the boundary of prosthesis 400 to provide strength and reduce the likelihood of sharp edges created by the porous structure, as best shown by FIG. 28B. Additionally, the rim 406 at the proximal end of prosthesis 400 may have a groove or a channel to receive bone cement or other adhesive in order to facilitate a firm connection between a joint prosthesis and prosthesis 400.

In an alternative embodiment, void filling prosthesis 400 may have a similar construction to that of body 302 of void filling prosthesis 300 such that the aperture 403 extends through the sidewall of prosthesis 400 at an anterior or posterior location. Such embodiment of prosthesis 400 may also have a curved portion with a similar frustoconical or cylindrical geometry, and a first and second wall portions that have similar planar or curved geometries. In such an embodiment, recesses 402 may extend through the first and second sidewalls to create space for the receipt of a tibial baseplate keel. This embodiment may be implanted into a tibia bone, while the opening formed in the sidewall by the aperture would allow the operator flexibility in positioning the stem so that a tibial baseplate connected thereto may be properly positioned on the proximal tibial resection.

Figure 29A:
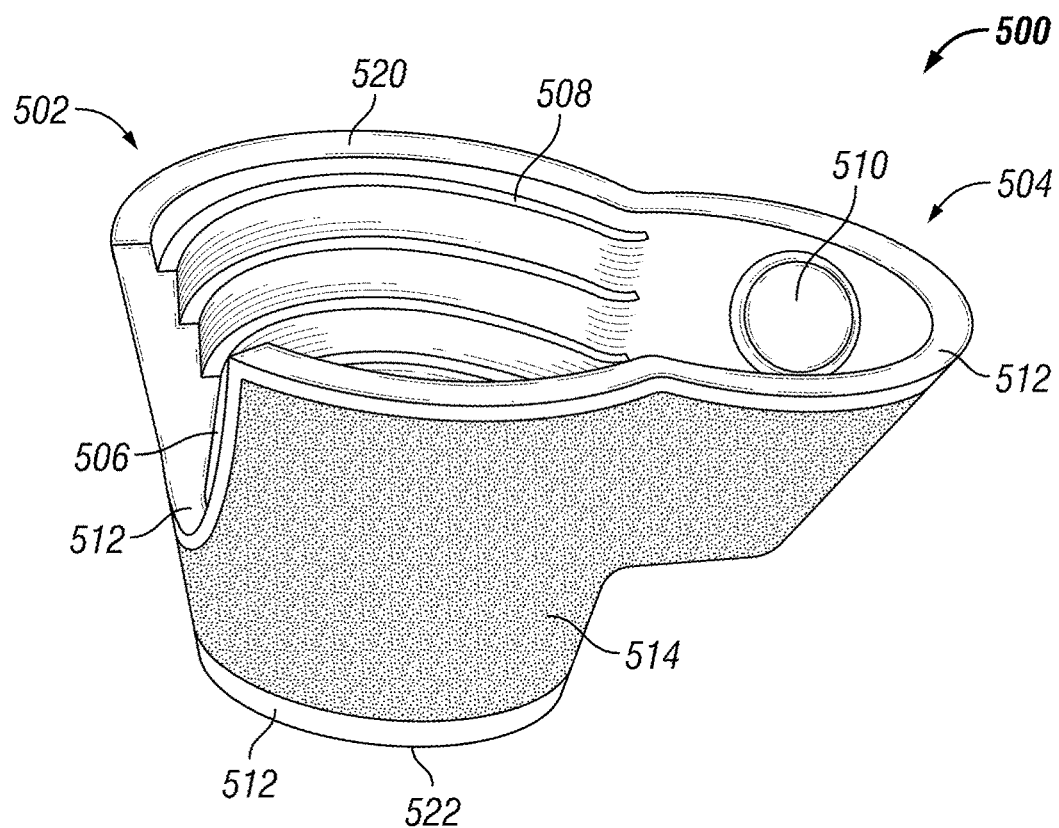
FIG. 29A is a front perspective of a further void filling prosthesis.

Prosthesis 500, as depicted in FIG. 29A, is similar to prosthesis 400, but differs in that prosthesis 500 includes a frustoconical lobe 504 portion for receipt of a keel of a joint prosthesis. Prosthesis 400 generally includes a body 502 and a lobe portion 504. The body 502 generally has a frustoconical profile, and the lobe portion 504 is generally a bump-out of the sidewall of the body 502 in the shape of a conical frustrum. Additionally, this lobe portion 504 has a central axis that is obliquely angled with respect to the central axis of the body 502. However, in some embodiments, these axes may be parallel. Also, in some embodiments, prosthesis 400 may include two lobe portions that are symmetrically arranged with body 504, which may be beneficial in addressing lateral and medial bone deformities. In some embodiments, one lobe may have a central axis parallel with the central axis of the body 502, and the other lobe portion may have a central axis obliquely angled with respect to the body 502.

In further embodiments, the aperture extending through body 502 may also extend through the sidewall of the body 502 at an anterior or posterior location much like that of body 302 of void filling prosthesis 300. Such opening formed in the sidewall would still allow for the lobe portion 504 and the recess 506 as the recess 506 and lobe portion 504 tend to be located more laterally and medially. This opening would also form a curved portion and a first and second wall portions much like that of body 302. However, in such an embodiment, the lobe portion 504 may be formed out of the first or second wall portion. Thus, in one embodiment, the curved portion could be cylindrical or frustoconical, the first wall portion could be planar or curved and have recess 506 extending therethrough, and the second wall portion could form lobe 504. In some circumstances where two lobe portions are desired, both the first and second wall portions can form the two lobe portions.

Figure 29B:
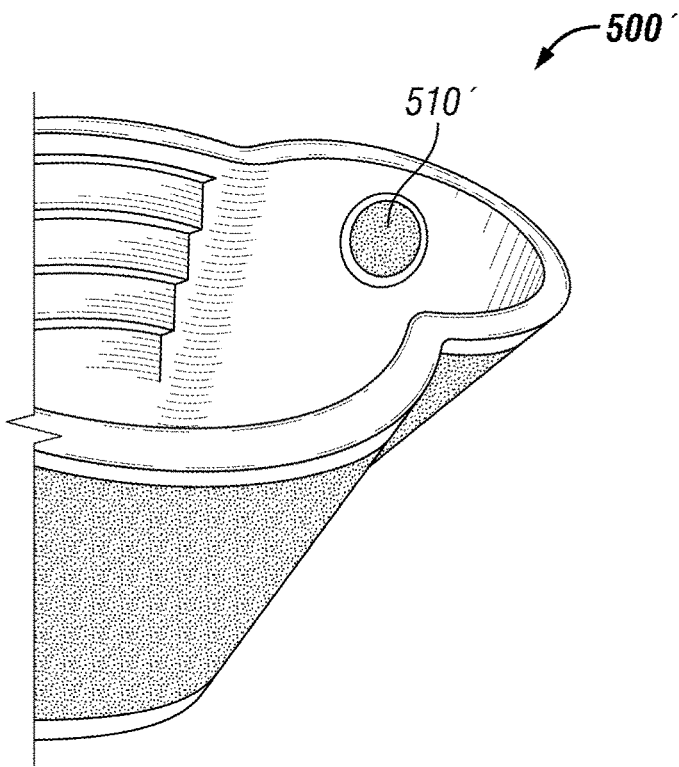
FIG. 29B is an alternative embodiment of the void filling prosthesis of FIG. 29A.

The lobe portion 504 may include an indented portion in its inner surface in order to accommodate large keels that extend into the inner surface of the lobe portion to prevent impingement of the prostheses. In some embodiments, as depicted in FIG. 29B, this indent may be a void in the inner surface of the lobe 504 such that the porous outer surface is exposed to the prosthesis aperture. This in and of itself may allow enough space for the prosthesis keel. However, where more space is desired, a cutting tool, such as a modified hole punch, may be utilized to remove the porous structure entirely from the void. Such features add to the universality of the prosthesis so as to reduce the number of resecting instruments and void filling prostheses in the operating room.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. Moreover, it will also be appreciated that the features described in connection with individual embodiments may be shared with others of the described embodiments.

The invention claimed is:

1. A method of replacing a distal femur, comprising:
removing a first femoral prosthesis previously implanted on the distal femur;
forming a bone void at an end of the distal femur;
inserting a void filling prosthesis into the bone void such that a body of the void filling prosthesis is positioned within the bone void and legs of the void filling prosthesis extending from the body are positioned entirely within the bone void, the body including an opening that extends through a sidewall of the body along an entire length of the body; and
implanting an intramedullary stem of a second femoral prosthesis through the opening that extends through the body and onto the distal femur after inserting the void filling prosthesis into the bone void.

2. The method of claim 1, wherein the forming step includes reaming the distal femur.

3. The method of claim 1, wherein the inserting step includes impacting the void filling prosthesis into the bone void in a press-fit fixation.

4. The method of claim 1, wherein the inserting step includes positioning the opening in the sidewall of the body within the bone void so that the opening faces an anterior direction.

5. The method of claim 4, wherein the inserting step is performed until an end surface of each leg is flush with or positioned beneath a resected surface of the distal femur.

6. The method of claim 5, wherein the implanting step includes positioning a cam box of the second femoral prosthesis within a space between the legs.

7. The method of claim 6, wherein the implanting step includes placing bone cement between an inner surface of the void filling prosthesis and the second femoral prosthesis.

8. A method of replacing a distal femur, comprising:
forming a bone void at an end of the distal femur;
inserting a void filling prosthesis into the bone void such that a body of the void filling prosthesis is positioned within the bone void and legs of the void filling prosthesis extending from the body are positioned within the bone void, the body having an opening extending through the body in a proximal-distal direction and through a sidewall thereof in an anterior direction, the opening extending through the sidewall along an entire length of the sidewall; and implanting a joint prosthesis onto the distal femur after inserting the void filling prosthesis into the bone void.

9. The method of claim 8, wherein the forming step includes reaming the distal femur with a reamer.

10. The method of claim 8, wherein the forming step includes forming the bone void such that it tapers inwardly in a distal to proximal direction.

11. The method of claim 8, wherein the implanting step includes inserting an intramedullary stem of the joint prosthesis through the opening in the body and positioning a femoral component of the joint prosthesis onto resected surfaces of the distal femur.

12. The method of claim 11, wherein each leg of the void filling prosthesis includes stepped surfaces, and the implanting step includes placing bone cement between the stepped surfaces and the femoral component.

13. The method of claim 8, wherein the inserting step is performed until an end surface of each leg is flush with or positioned proximal to a distal most resected surface of the distal femur.

14. The method of claim 8, wherein the implanting stem includes placing bone cement between an inner surface of the void filling prosthesis and the joint prosthesis.

15. A method of replacing a distal femur, comprising:
forming a bone void at an end of the distal femur;
inserting a void filling prosthesis into the bone void such that a body of the void filling prosthesis is positioned within the bone void and legs of the void filling prosthesis extending from the body are positioned within the bone void, the body having an opening extending through the body in a proximal-distal direction and through a sidewall thereof in an anterior direction; and
implanting a joint prosthesis onto the distal femur after inserting the void filling prosthesis into the bone void.

16. The method of claim 15, wherein the forming step includes reaming the distal femur with a reamer with a conical reamer such that at least a portion of the bone void has a shape corresponding to the conical reamer.

17. The method of claim 15, wherein the opening in the body extends through the sidewall along its entire length.

18. The method of claim 15, wherein the implanting step includes positioning a cam box of the second femoral prosthesis within a space between the legs.

19. The method of claim 15, wherein the inserting step includes impacting the void filling prosthesis into the bone void in a press-fit fixation so that the entire void filling prosthesis is positioned within the bone void.

\* \* \* \* \*